(12) United States Patent
Drummond et al.

(10) Patent No.: US 9,636,409 B2
(45) Date of Patent: May 2, 2017

(54) ENZYME AND RECEPTOR MODULATION USING COVALENT CONJUGATES OF ALPHA,ALPHA-DISUBSTITUTED GLYCINE ESTERS

(71) Applicant: GlaxoSmithKline Intellectual Property Development Limited, Brenford, Middlesex (GB)

(72) Inventors: Alan Hastings Drummond; Alan Hornsby Davidson, Abingdon (GB); David Festus Charles Moffat, Abingdon (GB); Alastair David Graham Donald, Oxfordshire (GB); Stephen John Davies, Abingdon (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 15/017,853

(22) Filed: Feb. 8, 2016

(65) Prior Publication Data

US 2016/0151509 A1 Jun. 2, 2016

Related U.S. Application Data

(63) Continuation of application No. 14/091,522, filed on Nov. 27, 2013, now abandoned, which is a continuation of application No. 12/867,455, filed as application No. PCT/GB2009/000561 on Feb. 27, 2009, now abandoned.

(30) Foreign Application Priority Data

Feb. 29, 2008 (GB) .................................. 0803747.5

(51) Int. Cl.

| | |
|---|---|
| ***C07D 211/70*** | (2006.01) |
| ***C07D 211/82*** | (2006.01) |
| ***C07D 213/55*** | (2006.01) |
| ***C07D 213/56*** | (2006.01) |
| ***A61K 31/44*** | (2006.01) |
| ***A61K 47/48*** | (2006.01) |
| ***C07D 213/73*** | (2006.01) |
| ***C12Q 1/48*** | (2006.01) |
| ***A61K 31/4418*** | (2006.01) |

(52) U.S. Cl.

CPC .... *A61K 47/48038* (2013.01); *A61K 31/4418* (2013.01); *C07D 213/73* (2013.01); *C12Q 1/485* (2013.01)

(58) Field of Classification Search

None

See application file for complete search history.

(56) References Cited

U.S. PATENT DOCUMENTS

| | | | | |
|---|---|---|---|---|
| 5,331,006 | A | 7/1994 | Horwell et al. | |
| 5,977,027 | A * | 11/1999 | Kawamura | A01N 43/36 504/242 |
| 7,932,246 | B2 | 4/2011 | Moffat et al. | |
| 7,939,666 | B2 | 5/2011 | Davidson et al. | |
| 7,973,181 | B2 | 7/2011 | Davidson et al. | |
| 8,003,695 | B2 | 8/2011 | Moffat et al. | |
| 8,044,211 | B2 | 10/2011 | Moffat et al. | |
| 8,106,091 | B2 | 1/2012 | Moffat et al. | |
| 8,148,531 | B2 | 4/2012 | Davidson et al. | |
| 8,211,900 | B2 | 7/2012 | Davidson | |
| 8,217,050 | B2 | 7/2012 | Moffat et al. | |
| 8,273,748 | B2 | 9/2012 | Kohno et al. | |
| 8,637,547 | B2 | 1/2014 | Davidson et al. | |
| 2005/0256102 | A1 | 11/2005 | Claiborne et al. | |
| 2009/0203711 | A1 | 8/2009 | Moffat | |
| 2009/0215800 | A1 | 8/2009 | Davidson et al. | |
| 2010/0004250 | A1 | 1/2010 | Philips et al. | |
| 2010/0010057 | A1 | 1/2010 | Moffat et al. | |
| 2010/0216802 | A1 | 8/2010 | Moffat et al. | |
| 2010/0267774 | A1 | 10/2010 | Moffat et al. | |
| 2010/0317678 | A1 | 12/2010 | Moffat et al. | |
| 2011/0034520 | A1 | 2/2011 | Moffat et al. | |
| 2012/0149736 | A1 | 6/2012 | Donald et al. | |
| 2013/0116318 | A1 | 5/2013 | Davidson et al. | |
| 2013/0197042 | A1 | 8/2013 | Davidson et al. | |
| 2013/0303576 | A1 | 11/2013 | Donald et al. | |

FOREIGN PATENT DOCUMENTS

| | | | |
|---|---|---|---|
| WO | 03/076405 | A1 | 9/2003 |
| WO | 2004/113336 | A1 | 12/2004 |

(Continued)

OTHER PUBLICATIONS

Carey, FA. Organic Chemistry 6th Ed. McGraw Hill. 2006, chapter 1, p. 9.*

(Continued)

*Primary Examiner* — Noble Jarrell

*Assistant Examiner* — Ben S Michelson

(74) *Attorney, Agent, or Firm* — Duke M. Fitch; Kathryn A. Lutomski; Edward R. Gimmi

(57) ABSTRACT

Covalent conjugates of an α,α-disubstituted glycine ester and a modulator of the activity of a target intracellular enzyme or receptor, wherein the ester group of the conjugate is hydrolysable by one or more intracellular carboxylesterase enzymes to the corresponding acid and the α,α-disubstituted glycine ester is conjugated to the modulator at a position remote from the binding interface between the inhibitor and the target enzyme or receptor pass into cells and the active acid hydrolysis product accumulates within the cells, as in the following compound:

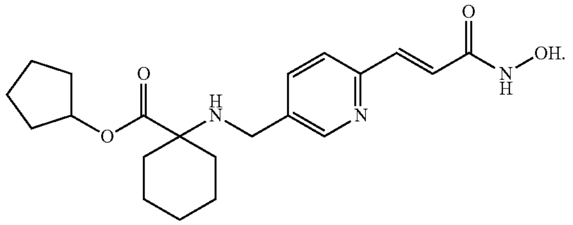

4 Claims, No Drawings

(56) References Cited

FOREIGN PATENT DOCUMENTS

| | | | | |
|---|---|---|---|---|
| WO | 2006/117567 | A1 | | 11/2006 |
| WO | WO 2006/117567 | A1 | * | 11/2006 |
| WO | 2007/129036 | A1 | | 11/2007 |
| WO | 2008/018447 | A1 | | 2/2008 |
| WO | 2008/040934 | A1 | | 4/2008 |
| WO | 2008/050341 | A2 | | 5/2008 |
| WO | 2009/023854 | A1 | | 2/2009 |
| WO | 2009/106844 | A1 | | 9/2009 |
| WO | 2009/130453 | A1 | | 10/2009 |

OTHER PUBLICATIONS

Yoshikawa, T. et al. Biotin Delivery to Brain with a Covalent Conjugate of Avidin and a Monoclonal Antibody to the Transferrin Receptor. JPET. 1992, vol. 263, p. 899.*
Connors, KV. et al. Some Derivatives of 1-aminocyclopentanecarboxylic acid and related compounds. Journal of the Chemical Society. 1960, p. 2119.*
F. A. Carey. Organic Chemistry, 6$^{th}$ Edition. McGraw Hill. Chapter 1, p. 9 (2006).
Yoshikawa, et al. JPET, 263: 899 (1992).
Dabrowska, et al. Biochemistry, 17: 253 (1978).
Connors, et al. Journal of the Chemical Society, pp. 2119 (1960).
Redinbo, et al. Drug Discover Today, 10(5): 313-325 (Mar. 2005).
Van Roon, et al. Arthritis & Rheumatism, 48(5): 1229-1238 (May 2003).
James R. O'Dell. New England Journal of Medicine, 350: 2591-2602 (2004).
Naldini, et al. Current Drug Targets—Inflammation & Allergy, 4: 3-8 (2005).
Nam, et al. Journal of Experimental Medicine, 201(3) Rockefeller University Press (2005).
Zhu, et al. Structure, 7(6): 651-661 (1999).
Jin, et al. The Journal of Biological Chemistry, 279(41): 42818-42825 (Oct. 8, 2004).
Huai, et al. Biochemistry, 42: 13220-13226 (2003).
Scapin, et al. Biochemistry, 43: 6091-6100 (2004).
Sintchak, et al. Cell, 85: 921-930 (1996).
Wang, et al. Structure, 6(9): 1117-1128 (1998).
Rowlinson, et al. The Journal of Biological Chemistry, 278(46): 45763-45769 (2003).
Schumacher, et al. J. Mol. Biol., 298: 875-893 (2000).
Chandra, et al. Biochemistry, 41: 10914-10919 (2002).
Essen, et al. Biochemistry, 36: 1704-1718 (1997).
Leiros, et al. J. Mol. Biol., 339: 805-820 (2004).
Rosenfeld, et al. Biochemistry, 41: 13915-13925 (2002).
Rudberg, et al. The Journal of Biological Chemistry, 279(26): 27376-27382 (2004).
Okamoto, et al. Chem. Pharm. Bull., 47(1): 11-21 (1999).
Bertrand, et al. J. Mol. Biol., 333: 393-407 (2003).
Louis, et al. Biochemistry, 37: 2105-2110 (1998).
Bressanelli, et al. PNAS, 96(23): 13034-13039 (1999).
Taylor, et al. J. Med. Chem., 41: 798-807 (1998).
Das, et al. J. Mol. Biol., 264: 1085-1100 (1996).
Khayat, et al. Biochemistry, 42: 885-891 (2003).
Champness, et al. Proteins, 32: 350-361 (1998).
Molteni, et al., Acta Cryst, D57: 536-544 (2001).
Harada, et al., Chem. Pharm. Bull., 45(7): 1156-1162 (1997).
Schirok, et al. J. Org. Chem., 70: 9463-9469 (2005).
Xu, et al. The Journal of Biological Chemistry, 279(48): 50401-50409 (2004).
Ruf, et al. Proc. Natl. Acad. Sci. USA, 93: 7481-7485 (1996).
Sheppard, et al. Bioorganic & Medicinal Chemistry Letters, 14: 865-868 (2004).
Bledsoe, et al. Cell, 110: 93-105 (2002).
Walker, et al. Molecular Cell, 6: 909-919 (2000).
Wan, et al. Cell, 116: 855-867 (2004).
Yang, et al. Nature Structural Biology, 9(12): 940-944 (2002).
Finnin, et al. Nature, 401: 188-193 (1999).
Nagar, et al. Cancer Research, 62: 4236-4243 (2002).
Munshi, et al. Acta Cryst, D59: 1725-1730 (2003).
Stout, et al. Structure, 6: 839-848 (1998).
Klein, et al. J. Mol. Biol., 249: 153-175 (1995).
Koelner, et al. J. Mol. Biol., 280: 153-166 (1998).
Hernandez-Guzman, et al. Journal of Biological Chemistry, 278(25): 22989-22997 (2003).
Stamos, et al. Journal of Biological Chemistry, 277(48): 46265-46272 (2002).
Lamers, et al. J. Mol. Biol., 285: 713-725 (1999).
McTigue, et al. Structure, 7(3): 319-330 (1999).
Hough, et al. J. Mol. Biol., 287: 579-592 (1999).
Almrud, et al. J. Mol. Biol., 295: 7-16 (2000).
Classen, et al. PNAS, 100(19): 10629-10634 (2003).
Staker, et al. PNAS, 99(24): 15387-15392 (2002).
Matias, et al. Journal of Biological Chemistry, 275(34): 26164-26171 (2000).
Heo, et al. EMBO, 23: 2185-2195 (2004).
Curtin, et al. Bioorganic & Medicinal Chemistry Letters, 13: 1367-1371 (2003).
Davis, et al. Science, 291: 134-137 (2001).
Gargaro, et al. J. Mol. Biol., 277: 119-134 (1998).
Griffith, et al. Molecular Cell, 13: 169-179 (2004).
Stams, et al. Protein Science, 7: 556-563 (1998).
Norman, et al. Structure, 12: 75-84 (2004).
Dobritzsch, et al. Journal of Biological Chemistry, 277(15): 13155-13166 (2002).
Van Den Elsen, et al. EMBO, 20(12): 3008-3017 (2001).
Ranganathan, et al. Cell, 89: 875-886 (1997).
Egea, et al. EMBO, 19(11): 2592-2601 (2000).
Jain, et al. Nature Structural Biology, 3(4): 375-380 (1996).
Oakley, et al. J. Mol. Biol., 291: 913-926 (1999).
Jez, et al. Chemistry & Biology, 10: 361-368 (2003).
Andersen, et al. Journal of Biological Chemistry, 275(10): 7101-7108 (2000).
Fancelli, et al. J. Med. Chem., 49: 7247-7251 (2006).
Komander, et al. Biochem. J., 375: 255-262 (2003).
Istvan, et al. Science, 292: 1160-1164 (May 11, 2001).
Lenhart, et al. Chemistry & Biology, 9: 639-645 (May 2002).
Mattevi, et al. Science, 255: 1544-1550 (1992).
Zhang, et al. Nature, 386: 247-253 (1997).
Ebdrup, et al. J. Med. Chem., 46: 1306-1317 (2003).
Bahnson, et al. Proc. Natl. Acad. Sci. USA, 94: 12797-12802 (1997).
Wei, et al. Nature Structural Biology, 6: 340-345 (1999).
Mathews, et al. Biochemistry, 37: 15607-15620 (1998).
Urzhumtsev, et al. Structure, 5: 601-612 (1997).
Tocchini-Valentini, et al. PNAS, 98: 5491-5496 (2001).
Gene expression CES1 (or hCE-1, CES1A1), http://biogps.org/#goto=welcome, search term CES1, human gene, graphical representation of distribution in tissue rather than cell, Oct. 12, 2013.

* cited by examiner

ENZYME AND RECEPTOR MODULATION USING COVALENT CONJUGATES OF ALPHA,ALPHA-DISUBSTITUTED GLYCINE ESTERS

CROSS REFERENCE TO RELATED APPLICATIONS

This application is a Continuation of application Ser. No. 14/091,522, filed 27 Nov. 2013, which is a Continuation of application Ser. No. 12/867,455, filed 12 Aug. 2010 (abandoned), which is a 371 of International Application No. PCT/GB2009/000561, filed 27 Feb. 2009, which claims priority to UK Application No. 0803747.5, filed 29 Feb. 2008.

This invention relates to a general method of increasing or prolonging the activity of a compound which modulates the activity of an Intracellular enzyme or receptor by the covalent conjugation of an α,α-disubstituted glycine ester motif to the modulator. The invention also relates to modulators to which an α,α-disubstituted glycine ester motif has been covalently conjugated, and to a method for the Identification of such conjugates having superior properties relative to the parent non-conjugated modulator. The Invention further relates to the use of modulators containing α,α-disubstituted glycine ester motifs that allow the selective accumulation of amino acid conjugates inside cells of the monocyte-macrophage lineage.

BACKGROUND TO THE INVENTION

Many intracellular enzymes and receptors are targets for pharmaceutically useful drugs which modulate their activities by binding to their active sites. Examples appear in Table 1 below. To reach the target enzymes and receptors, modulator compounds must of course cross the cell membrane from plasma/extracellular fluid. In general, charge neutral modulators cross the cell membrane more easily than charged species. A dynamic equilibrium is then set up whereby the modulator equilibrates between plasma and cell interior. As a result of the equilibrium, the intracellular residence times and concentrations of many modulators of intracellular enzymes and receptors are often very low, especially in cases where the modulator is rapidly cleared from the plasma. The potencies of the modulators are therefore poor despite their high binding affinities for the target enzyme or receptor.

Our International Patent Application WO 2006/117567 discloses a method for increasing the intracellular concentration of a given modulator of an intracellular enzyme or receptor by conjugating thereto an α-amino acid ester motif which is hydrolysed by one or more of the intracellular carboxylesterases hCE-1, hCE-2 and hCE-3. This results in increased potency by prolonging the residency of the modulator inside the cell, and leads to improved pharmacokinetic and pharmacodynamic properties. More consistent exposure and reduced dosing frequencies can be achieved. A further benefit is obtained when the α-amino add ester motif is conjugated to the modulator such that the drug is targeted to the specific target cells responsible for its therapeutic action, reducing systemic exposure and hence side effects.

The α-amino add ester conjugates disclosed in International Patent Application WO 2006/117567 are all monosubstituted on the α-carbon. That publication does not suggest that α,α-disubstituted glycine ester conjugates can be hydrolysed by intracellular carboxylesterases. In fact, it appears that the ability of the intracellular carboxyl esterases, principally hCE-1, hCE-2 and hCE-3, to hydrolyse α,α-disubstituted glycine ester has not previously been investigated.

BRIEF DESCRIPTION OF THE INVENTION

This invention is based on the novel finding that conjugates of α,α-disubstituted glycine esters can be hydrolysed by intracellular carboxyl esterases, and thus the methods and benefits described in WO 2006/117567 can also be obtained with such conjugates. Such benefits include intracellular accumulation of the acid hydrolysis product, and in some cases selective accumulation in cells of a particular type. As in the case of WO 2006/117567, the present invention takes advantage of the fact that lipophilic (low polarity or charge neutral) molecules pass through the cell membrane and enter cells relatively easily, and hydrophilic (higher polarity, charged) molecules do not. Hence, if a lipophilic motif is attached to a given modulator, allowing the modulator to enter the cell, and if that motif is converted in the cell to one of higher polarity, it is to be expected that the modulator with the higher polarity motif attached would accumulate within the cell. Providing such a motif is attached to the modulator in a way which does not alter its binding mode with the target enzyme or receptor, the accumulation of modulator with the higher polarity motif attached is therefore expected to result in prolonged and/or increased activity.

As in the case of WO 2006/117567, the present invention makes use of the fact that there are carboxylesterase enzymes within cells, which may be utilised to hydrolyse an α,α-disubstituted glycine ester motif attached to a given modulator to the parent acid. Therefore, a modulator may be administered as a covalent conjugate with an α,α-disubstituted glycine ester, in which form it readily enters the cell where it is hydrolysed efficiently by one or more intracellular carboxylesterases, and the resultant α,α-disubstituted glycine-modulator conjugate accumulates within the cell, increasing overall potency and/or active residence time. It has also been found that by modification of the α,α-disubstituted glycine ester motif or the way in which it is conjugated, modulators can be targeted to monocytes and macrophages. Herein, unless “monocyte” or “monocytes” is specified, the term macrophage or macrophages will be used to denote macrophages (including tumour associated macrophages) and/or monocytes.

DETAILED DESCRIPTION OF THE INVENTION

Hence in one broad aspect the present invention provides a covalent conjugate of an α,α-disubstituted glycine ester and a modulator of the activity of a target intracellular enzyme or receptor, wherein: the ester group of the conjugate is hydrolysable by one or more intracellular carboxylesterase enzymes to the corresponding acid; and the α,α-disubstituted glycine ester is covalently attached to the modulator at a position remote from the binding interface between the modulator and the target enzyme or receptor, and/or is conjugated to the modulator such that the binding mode of the conjugated modulator and the said corresponding acid to the target enzyme or receptor is the same as that of the unconjugated modulator.

Looked at in another way, the invention provides a method of increasing or prolonging the intracellular potency and/or residence time of a modulator of the activity of a target intracellular enzyme or receptor comprising structural modification of the modulator by covalent attachment thereto of an α,α-disubstituted glycine ester at a position remote from the binding interface between the modulator and the target enzyme or receptor, and/or such that the binding mode of the conjugated modulator and the said corresponding acid to the target enzyme or receptor is the same as that of the unconjugated modulator, the ester group of the conjugate being hydrolysable by one or more intracellular carboxylesterase enzymes to the corresponding acid.

By covalently attaching the α,α-disubstituted glycine ester part to the modulator such that the binding mode of the modulator to the target enzyme or receptor is preserved, both the ester conjugate and the corresponding acidic α,α-disubstituted glycine conjugate retain the modulator activity of the parent unconjugated modulator. The absolute enzyme inhibitory potencies or the receptor agonist or antagonist potencies of the ester and acid conjugates need not necessarily be as high as the corresponding potencies of the unconjugated modulator, since intracellular hydrolysis of the ester conjugate to the acid conjugate results in an accumulation of the latter within the cell, and the resultant concentration of the acid conjugate within the cell is higher than that achievable with the unconjugated modulator, thereby compensating for any intrinsically lower potency of the former relative to the latter. It will therefore be apparent that the conjugation strategy of the present invention differs from the traditional "pro-drug" approach. In the traditional "prodrug" approach, the parent modulator would be modified by conversion to a derivative which is processed in vivo to release the original modulator, and it is the release of the original modulator which is responsible for the ultimate activity. In the present strategy, the original modulator is modified so that the eventual activity is the combined result of intracellular activity due to the α,α-disubstituted glycine conjugate of the modulator, and the accumulating α,α-disubstituted glycine conjugate of the modulator. The active species is a conjugate, not the original unconjugated modulator.

As stated, the invention is concerned with modification of modulators of intracellular enzymes or receptors. Although the principle of the invention is of general application, not restricted by the chemical identity of the modulator or the identity of the target enzyme or receptor, it is strongly preferred that the modulator be one that exerts its effect by reversible binding to the target enzyme or receptor, as opposed to those whose effect is due to covalent binding to the target enzyme or receptor.

Since for practical utility the carboxylesterase-hydrolysed conjugate is required to retain the intracellular binding activity of the parent modulator with its target enzyme or receptor, attachment of the ester motif must take account of that requirement, which will be fulfilled if the carboxylesterase-hydrolysable α,α-disubstituted glycine ester motif is attached to the modulator such that the binding mode of the corresponding carboxylesterase hydrolysis product (ie the corresponding acid) to the target is essentially the same as the unconjugated modulator. In general this is achieved by covalent attachment of the carboxylesterase ester motif to the modulator at a position remote from the binding interface between the modulator and the target enzyme or receptor. In this way, the motif is arranged to extend into solvent, rather than potentially interfering with the binding mode, In addition, the α,α-disubstituted glycine ester motif obviously must be a substrate for the carboxylesterase if the former is to be hydrolysed by the latter within the cell. The ability of intracellular carboxylesterases appears not to depend on very strict structural requirements of the α,α-disubstituted glycine ester substrate. Hence most modes of covalent conjugation of the α,α-disubstituted glycine ester motif to a modulator will allow hydrolysis. Attachment by a flexible linker chain will usually be how this is achieved.

It will be appreciated that any chemical modification of a drug may subtly alter its binding geometry, and the chemistry strategy for linkage of the α,α-disubstituted glycine ester carboxylesterase motif may introduce additional binding interactions with the target, or may substitute for one or more such interactions. Hence the requirement that the hydrolysed conjugate's binding mode to the target is the same as the unconjugated modulator is to be interpreted as requiring that there is no significant perturbation of the binding mode, in other words that the binding mode is essentially the same as that of the unconjugated modulator. When the requirement is met, the main binding characteristics of the parent modulator are retained, and the modified and unmodified modulators have an overall common set of binding characteristics. The "same binding mode" and "remote attachment" viewpoints are similar because, as stated above, the usual way of achieving the "same binding mode" requirement is to attach the carboxylesterase motif at a point in the modulator molecule which is remote from the binding interface between the Inhibitor and the target enzyme or receptor. However, it should be noted that these requirements do not imply that the conjugate and/or its corresponding acid must have the same in vitro or in vivo modulatory potency as the parent modulator. In general, however, it is preferred that the esterase-hydrolysed carboxylic acid has a potency in an in vitro enzyme- or receptor-binding assay no less than one tenth of the potency of the parent modulator in that assay, and that the ester has a potency in a cellular activity assay at least as high as that of the parent modulator in the same assay.

Although traditional medicinal chemistry methods of mapping structure-activity relationships are perfectly capable of identifying an attachment strategy to meet the foregoing "same binding mode" and "remote attachment" requirements, modern techniques such as NMR and X-ray crystallography have advanced to the point where it is very common for the binding mode of a known modulator of an enzyme or receptor to be known, or determinable. Such information is in the vast majority of cases in the public domain, or can be modelled using computer based modelling methods, such as ligand docking and homology modelling, based on the known binding modes of structurally similar modulators, or the known structure of the active site of the target enzyme or receptor. With knowledge of the binding mode of the modulator obtained by these techniques, a suitable location for attachment of the carboxylesterase ester motif may be identified, usually (as stated above) at a point on the modulator which is remote from the binding interface between the inhibitor and the target enzyme or receptor.

Intracellular carboxylesterase enzymes capable of hydrolysing the ester group of the conjugated alpha amino acid to the corresponding acid include the three known human carboxylesterase ("hCE") enzyme isotypes hCE-1 (also known as CES-1), hCE-2 (also known as CES-2) and hCE-3 (Drug Disc. Today 2005, 10, 313-325). Although these are considered to be the main enzymes other carboxylesterase enzymes such as biphenylhydrolase (BPH) may also have a role in hydrolysing the conjugates.

The broken cell assay described below is a simple method of confirming that a given conjugate of modulator and α,α-disubstituted glycine ester, or a given α,α-disubstituted glycine ester to be assessed as a possible carboxylesterase ester motif, is hydrolysed as required. These enzymes can also be readily expressed using recombinant techniques, and the recombinant enzymes may be used to determine or confirm that hydrolysis occurs.

It is a feature of the invention that the desired conjugate retains the covalently linked α,α-disubstituted glycine add motif when hydrolysed by the carboxylesterase(s) within the cell, since it is the polar carboxyl group of that motif which prevents or reduces clearance of the hydrolysed conjugate from the cell, and thereby contributes to its accumulation within the cell. Indeed, the cellular potency of the modified modulator is predominantly due to the accumulation of the acid and its modulation of the activity of the target (although the unhydrolysed ester also exerts its activity on the target for so long as it remains unhydrolysed). Since cells in general contain several types of peptidase enzymes, it is preferable that the conjugate, or more especially the hydrolysed conjugate (the corresponding add), is not a substrate for such peptidases. In particular, it is strongly preferred that the α,α-disubstituted glycine ester group should not be the C-terminal element of a dipeptide motif in the conjugate. However, apart from that limitation on the mode of covalent attachment, the α,α-disubstituted glycine ester group may be covalently attached to the modulator via its amino group or via its one of the α-substituents. In some cases the modulator will have a convenient point of attachment for the carboxylesterase ester motif, and in other cases a synthetic strategy will have to be devised for its attachment.

It has been found that cells that only express the carboxylesterases hCE-2, and/or hCE-3 and recombinant forms of these enzymes will only hydrolyse α,α-disubstituted glycine esters to their resultant adds if the amino nitrogen of the α,α-disubstituted glycine ester is either unsubstituted or is directly linked to a carbonyl group (ie the amino group forms part of an amide motif), whereas cells containing hCE-1 (ie macrophages), or recombinant hCE-1, can hydrolyse α,α-disubstituted glycine esters with a wide range of groups on the nitrogen. This selectivity requirement of hCE-2 and hCE-3 can be turned to advantage where it is required that the modulator should target enzymes or receptors in certain cell types only. The relative amounts of these three carboxylesterase enzymes vary between cell types (see FIG. 1 of WO 2006/117567 and database at http:/symatlas.gnf.org/SymAtlas (note that in this database hCE3/CES3 is referred to by the symbol FLJ21736)). If the modulator is intended to act only in cell types where hCE-1 is found, attachment of the α,α-disubstituted glycine ester carboxylesterase ester motif in such a way that the amino group is not directly attached to a carbonyl, results in the hydrolysed modulator conjugate accumulating preferentially in cells with effective concentrations of hCE-1. Stated in another way, specific accumulation of the acid derived from the modulator conjugate in hCE-1 expressing cells can be achieved by linking the amino acid ester motif to the modulator in such a way that the nitrogen atom of the amino acid ester is not linked directly to a carbonyl, or is left unsubstituted.

Macrophages are known to play a key role in inflammatory disorders through the release of cytokines in particular TNFα and IL-1 (van Roon et al Arthritis and Rheumatism, 2003, 1229-1238). In rheumatoid arthritis they are major contributors to joint inflammation and joint destruction (Conell in N. Eng J. Med. 2004, 350, 2591-2602). Macrophages are also involved in tumour growth and development (Naldini and Carraro in Curr Drug Targets Inflamm Allergy, 2005, 3-8). Hence agents that selectively target macrophage cells could be of value in the treatment of cancer, inflammation and autoimmune disease. Targeting specific cell types would be expected to lead to reduced side-effects. The present invention enables a method of targeting modulators to macrophages, which is based on the above observation that the way in which the α,α-disubstituted glycine ester carboxylesterase ester motif is linked to the modulator determines whether it is hydrolysed by specific carboxylesterases, and hence whether or not the resultant acid accumulates in different cell types.

Specifically, as disclosed in WO 2006/117567, it has been found that macrophages contain the human carboxylesterase hCE-1 whereas other cell types do not. In the conjugates of the invention, when the nitrogen of the ester motif is substituted but not directly bonded to a carbonyl group moiety the ester will only be hydrolysed by hCE-1 and hence the esterase-hydrolysed modulator conjugates will only accumulate in macrophages.

Furthermore, the α,α-disubstituted glycine conjugates of the invention are in general more potent in cells containing the carboxylesterase HCE-1 (ie macrophages) than in cells which only contain the carboxylesterases HCE-2 and HCE-3.

Also, it has been found that conjugates of the invention in which the α,α-disubstituted glycine ester motif is linked to the modulator via one of the α substituents of the α,α-disubstituted glycine ester are in general more potent in cells containing the carboxylesterase HCE-1 (ie macrophages) than in cells which only contain the carboxylesterases HCE-2 and HCE-3. The active hydrolysed acid conjugate therefore accumulates non-selectively in the case of such (generally) C-linked ester conjugates.

TERMINOLOGY

As used herein, the term "α,α-disubstituted glycine" or "α,α-disubstituted glycine acid" means a compound of formula $H_2N—C(R_2R_3)—COOH$, wherein $R_2$ and $R_3$ represent the α-substituents (which of course are not hydrogen), and an "α,α-disubstituted glycine ester is such a compound wherein the carboxylic add group is esterified. The term "ester" or "esterified carboxyl group" means a group $R_9O(C{=}O)—$ in which $R_9$ is the group characterising the ester, notionally derived from the alcohol $R_9OH$.

As used herein, the term "$(C_a-C_b)$alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "divalent $(C_a-C_b)$alkylene radical" wherein a and b are integers refers to a saturated hydrocarbon chain having from a to b carbon atoms and two unsatisfied valences.

As used herein the term "$(C_a-C_b)$alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "divalent $(C_a-C_b)$alkenylene radical" means a hydrocarbon chain having from a to b carbon atoms, at least one double bond, and two unsatisfied valences.

As used herein the term "$(C_a-C_b)$alkynyl" wherein a and b are integers refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent ($C_a$-$C_b$)alkynylene radical" wherein a and b are integers refers to a divalent hydrocarbon chain having from 2 to 6 carbon atoms, and at least one triple bond.

As used herein the term "carbocyclic" refers to a mono-, bridged mono-, bi- or tricyclic radical having up to 16 ring atoms, all of which are carbon, and includes aryl and cycloalkyl.

As used herein the term "cycloalkyl" refers to a monocyclic saturated carbocylic radical having from 3-8 carbon atoms and includes, for example, cyclopropyl, cyclobutyl, cyclopentyl, cyclohexyl, cycloheptyl, cyclooctyl and norbornyl.

As used herein the unqualified term "aryl" refers to a mono-, bridged mono-, bi- or tri-cyclic carbocyclic aromatic radical, and includes radicals having two monocyclic carbocyclic aromatic rings which are directly linked by a covalent bond. Illustrative of such radicals are phenyl, biphenyl and napthyl.

As used herein the unqualified term "heteroaryl" refers to a mono-, bridged mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocylic" includes "heteroaryl" as defined above, and in its non-aromatic meaning relates to a mono-, bridged mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "optionally substituted" as applied to any moiety herein means such moiety may be substituted with up to four compatible substituents, each of which independently may be, for example, ($C_1$-$C_6$)alkyl, ($C_1$-$C_6$)alkoxy, hydroxy, hydroxy($C_1$-$C_6$)alkyl, mercapto, mercapto($C_1$-$C_6$) alkyl, ($C_1$-$C_6$)alkylthio, phenyl, halo (including fluoro, bromo and chloro), trifluoromethyl, trifluoromethoxy, nitro, nitrile (—CN), oxo, —COOH, —$COOR^A$, —$COR^A$, —$SO_2R^A$, —$CONH_2$, —$SO_2NH_2$, —$CONHR^A$, —$SO_2NHR^A$, —$CONR^AR^B$, —$SO_2NR^AR^B$, —$NH_2$, —$NHR^A$, —$NR^AR^B$, —$OCONH_2$, —$OCONHR^A$, —$OCONR^AR^B$, —$NHCOR^A$, —$NHCOOR^A$, —$NR^B$-$COOR^A$, —$NHSO_2OR^A$, —$NR^BSO_2OH$, —$NR^BSO_2OR^A$, —$NHCONH_2$, —$NR^ACONH_2$, —$NHCONHR^B$, —$NR^A$-$CONHR^B$, —$NHCONR^AR^B$, or —$NR^ACONR^AR^B$ wherein $R^A$ and $R^B$ are independently a ($C_1$-$C_6$)alkyl, ($C_3$-$C_6$)cycloalkyl, phenyl or monocyclic heteroaryl having 5 or 6 ring atoms, or $R^A$ and $R^B$ when attached to the same nitrogen atom form a cyclic amino group (for example morpholino, piperidinyl, piperazinyl, or tetrahydropyrrolyl). An "optional substituent" may be one of the foregoing substituent groups.

The term "side chain of a natural or non-natural alpha-amino add" refers to the group $R^1$ in a natural or non-natural amino acid of formula $NH_2$—$CH(R^1)$—COOH, other than glycine, in which $R^1$ is hydrogen.

Examples of side chains of natural alpha amino acids include those of alanine, arginine, asparagine, aspartic acid, cysteine, cysteine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic add, α-amino-n-butyric acid, 3,4-dihydroxyphenylalanine, homoserine, α-methylserine, omithine, pipecolic add, and thyroxine.

Natural alpha-amino acids which contain functional substituents, for example amino, carboxyl, hydroxy, mercapto, guanidyl, imidazolyl, or indolyl groups in their characteristic side chains include arginine, lysine, glutamic acid, aspartic acid, tryptophan, histidine, serine, threonine, tyrosine, and cysteine. When one or both of the α-substituents in the α,α-disubstituted glycine ester motif in the compounds of the Invention is one of those side chains, the functional substituent may optionally be protected.

The term "protected" when used in relation to a functional substituent in a side chain of a natural alpha-amino acid means a derivative of such a substituent which is substantially non-functional. For example, carboxyl groups may be esterified (for example as a $C_1$-$C_6$ alkyl ester), amino groups may be converted to amides (for example as a $NHCOC_1$-$C_6$ alkyl amide) or carbamates (for example as an NHC(=O) $OC_1$-$C_6$ alkyl or NHC(=O)$OCH_2$Ph carbamate), hydroxyl groups may be converted to ethers (for example an $OC_1$-$C_6$ alkyl or a O($C_1$-$C_6$ alkyl)phenyl ether) or esters (for example a OC(=O)$C_1$-$C_6$ alkyl ester) and thiol groups may be converted to thioethers (for example a tert-butyl or benzyl thioether) or thioesters (for example a SC(=O)$C_1$-$C_6$ alkyl thioester).

There are many possible ester groups which may in principle be present in the α,α-disubstituted glycine ester carboxylesterase ester motif for attachment to the modulator. Likewise, there are many α,α-disubstituted glycines, differing in the α-substituents $R_2$ and $R_3$, which may be used as esters in the carboxylesterase ester motif. Some α,α-disubstituted glycine esters are rapidly hydrolysed by one or more of the hCE-1, -2 and -3 Isotypes or cells containing these enzymes, while others are more slowly hydrolysed, or hydrolysed only to a very small extent. In general, if the carboxylesterase hydrolyses the free α,α-disubstituted glycine ester to the parent acid it will, subject to the N-carbonyl dependence of hCE-2 and hCE-3 discussed above, also hydrolyse the ester motif when covalently conjugated to the modulator. Hence, the broken cell assay and/or the isolated carboxylesterase assay described herein provide a straightforward, quick and simple first screen for esters which have the required hydrolysis profile. Ester motifs selected in that way may then be re-assayed in the same carboxylesterase assay when conjugated to the modulator via the chosen conjugation chemistry, to confirm that it is still a carboxylesterase substrate in that background.

The Ester Group

As mentioned, intracellular carboxylesterase enzymes capable of hydrolysing the ester group of a compound of the invention to the corresponding acid include the three known human enzyme isotypes hCE-1, hCE-2 and hCE-3. Although these are considered to be the main enzymes, other enzymes such as biphenylhydrolase (BPH) may also have a role in hydrolysing the ester. In general, if the carboxylesterase hydrolyses the free amino acid ester to the parent acid it will also hydrolyse the ester motif when covalently conjugated to the Inhibitor. Hence, the broken cell, assay and/or the isolated carboxylesterase assay described herein provide a straightforward, quick and simple first screen for esters which have the required hydrolysis profile. Ester motifs selected in that way may then be re-assayed in the same carboxylesterase assay when conjugated to the Inhibitor via the chosen conjugation chemistry, to confirm that it is still a carboxylesterase substrate in that background.

Subject to the requirement that they be hydrolysable by intracellular carboxylesterase enzymes, examples of particular ester groups in the α,α-disubstituted glycine ester carboxylesterase ester motif include those of formula —(C═O)OR$_{14}$ wherein R$_{14}$ is R$_8$R$_9$R$_{10}$C— wherein (i) R$_8$ is hydrogen or optionally substituted (C$_1$-C$_3$)alkyl-(Z$^1$)$_a$—[(C$_1$-C$_3$)alkyl]$_b$- or (C$_2$-C$_3$)alkenyl-(Z$^1$)$_a$—[(C$_1$-C$_3$)alkyl]$_b$- wherein a and b are independently 0 or 1 and Z$^1$ is —O—, —S—, or —NR$_{11}$— wherein R$_{11}$ is hydrogen or (C$_1$-C$_3$)alkyl; and R$_9$ and R$_{10}$ are independently hydrogen or (C$_1$-C$_3$)alkyl-;

(ii) R$_8$ is hydrogen or optionally substituted R$_{12}$R$_{13}$N—(C$_1$-C$_3$)alkyl- wherein R$_{12}$ is hydrogen or (C$_1$-C$_3$)alkyl and R$_{13}$ is hydrogen or (C$_1$-C$_3$)alkyl; or R$_{12}$ and R$_{13}$ together with the nitrogen to which they are attached form an optionally substituted monocyclic heterocylic ring of 5- or 6-ring atoms or bicyclic heterocyclic ring system of 8 to 10 ring atoms, and R$_9$ and R$_{10}$ are independently hydrogen or (C$_1$-C$_3$)alkyl-; or (iii) R$_8$ and R$_9$ taken together with the carbon to which they are attached form an optionally substituted monocyclic or bridged monocyclic carbocylic ring of from 3 to 7 ring atoms or bicyclic or bridged monocyclic carbocyclic ring system of 8 to 10 ring atoms, and R$_{10}$ is hydrogen.

In cases (i), (II) and (ii) above, "alkyl" includes fluoroalkyl.

Within these classes (i), (ii) and (III), R$_{10}$ is often hydrogen. Specific examples of R$_{14}$ include methyl, trifluoromethyl, ethyl, n- or iso-propyl, n-, sec- or tert-butyl, cyclohexyl, norbornyl, allyl, phenyl, benzyl, 2-, 3- or 4-pyridylmethyl, N-methylpiperidin-4-yl, tetrahydrofuran-3-yl or methoxyethyl. Currently preferred is where R$_{14}$ is cyclopentyl.

α-Substituents

Examples of α-substituents R$_2$ and R$_3$ of the α,α-disubstituted glycine ester conjugated to the modulator may be regarded as selected from the side chains of a natural or non-natural alpha-amino add, and in such side chains any functional groups may be protected.

For example, α-substituents R$_2$ and R$_3$ of the α,α-disubstituted glycine ester conjugated to the modulator include phenyl and groups of formula —CR$_a$R$_b$R$_c$ in which:

each of R$_a$, R$_b$ and R$_c$ is independently hydrogen, (C$_1$-C$_6$)alkyl, (C$_2$-C$_6$)alkenyl, (C$_2$-C$_6$)alkynyl, phenyl(C$_1$-C$_6$)alkyl, (C$_3$-C$_8$)cycloalkyl; or R$_c$ is hydrogen and R$_a$ and R$_b$ are independently phenyl or heteroaryl such as pyridyl; or R$_c$ is hydrogen, (C$_1$-C$_6$)alkyl, (C$_2$-C$_6$)alkenyl, (C$_2$-C$_6$)alkynyl, phenyl(C$_1$-C$_6$)alkyl, or (C$_3$-C$_8$)cycloalkyl, and R$_a$ and R$_b$ together with the carbon atom to which they are attached form a 3 to 8 membered cycloalkyl or a 5- to 6-membered heterocyclic ring; or R$_a$, R$_b$ and R$_c$ together with the carbon atom to which they are attached form a tricyclic ring (for example adamantyl; or R$_a$ and R$_b$ are each independently (C$_1$-C$_6$)alkyl, (C$_2$-C$_6$)alkenyl, (C$_2$-C$_6$)alkynyl, phenyl(C$_1$-C$_6$)alkyl, or a group as defined for R$_c$ below other than hydrogen, or R$_a$ and R$_b$ together with the carbon atom to which they are attached form a cycloalkyl or heterocyclic ring, and R$_c$ is hydrogen, —OH, —SH, halogen, —CN, —CO$_2$H, (C$_1$-C$_4$)perfluoroalkyl, —CH$_2$OH, —O(C$_1$-C$_6$)alkyl, —O(C$_2$-C$_6$)alkenyl, —S(C$_1$-C$_6$)alkyl, —SO(C$_1$-C$_6$)alkyl, —SO$_2$(C$_1$-C$_6$)alkyl, —S(C$_2$-C$_6$)alkenyl, —SO(C$_2$-C$_6$)alkenyl, —SO$_2$(C$_2$-C$_6$)alkenyl or a group -Q-W wherein Q represents a bond or —O—, —S—, —SO— or —SO— and W represents a phenyl, phenylalkyl, (C$_3$-C$_8$)cycloalkyl, (C$_3$-C$_8$)cycloalkylalkyl, (C$_4$-C$_8$)cycloalkenyl, (C$_4$-C$_8$)cycloalkenylalkyl, heteroaryl or heteroarylalkyl group, which group W may optionally be substituted by one or more substituents independently selected from, hydroxyl, halogen, —CN, —CONH$_2$, —CONH(C$_1$-C$_6$)alkyl, —CONH(C$_1$-C$_6$alkyl)$_2$, —CHO, —CH$_2$OH, (C$_1$-C$_4$)perfluoroalkyl, —O(C$_1$-C$_6$)alkyl, —S(C$_1$-C$_6$)alkyl, —SO(C$_1$-C$_6$)alkyl, —SO$_2$(C$_1$-C$_6$)alkyl, —NO$_2$, —NH$_2$, —NH(C$_1$-C$_6$)alkyl, —N((C$_1$-C$_6$)alkyl)$_2$, —NHCO(C$_1$-C$_6$)alkyl, (C$_1$-C$_6$)alkyl, (C$_2$-C$_6$)alkenyl, (C$_2$-C$_6$)alkynyl, (C$_3$-C$_8$)cycloalkyl, (C$_4$-C$_8$)cycloalkenyl, phenyl or benzyl.

Alternatively, the α-substituents R$_2$ and R$_3$ of the α,α-disubstituted glycine ester conjugated to the modulator, taken together with the α-carbon itself, may form a 3-6 membered saturated cycloalkyl ring, such as a cyclopropyl, cyclopentyl or cyclohexyl ring or heterocyclyl ring such as a piperidin-4-yl ring.

In some cases, at least one of the α-substitutents R$_2$ and R$_3$ of the α,α-disubstituted glycine ester conjugated to the modulator is a C$_1$-C$_6$ alkyl substituent, for example methyl, ethyl, or n- or iso-propyl.

In some embodiments, one of the α-substitutents R$_2$ and R$_3$ of the α,α-disubstituted glycine ester conjugated to the modulator is a C$_1$-C$_6$ alkyl substituent, for example methyl, ethyl, or n- or isopropyl, and the other is selected from the group consisting of methyl, ethyl, n- and iso-propyl, n-, sec- and tert-butyl, phenyl, benzyl, thienyl, cyclohexyl, and cyclohexylmethyl.

Currently preferred are cases where one of R$_2$ and R$_3$ is methyl, and the other is methyl, ethyl, or n- or iso-propyl; or where R$_2$ and R$_3$ taken together with the carbon to which they are attached form a cyclopropyl, cyclobutyl, cyclopentyl or cyclohexyl ring. In a particular case, the α-substitutents R$_2$ and R$_3$ of the α,α-disubstituted glycine ester conjugated to the modulator are each methyl.

Conjugation

As stated above, the α,α-disubstituted glycine ester may be conjugated to the modulator via its amino group, or via one of the α-substituents. A linker radical may be present between the carboxylesterase ester motif and the modulator. The structure of the radical linking the carboxylesterase ester motif to the rest of the modulator obviously depends on the particular chemistry strategy chosen for such linkage. Clearly the chemistry strategy for that coupling may vary widely, and thus many linkage structures are possible. The precise combination of variables making up the linking chemistry between the amino acid ester motif and the rest of the molecule will often be irrelevant to the primary binding mode of the compound as a whole. On the other hand, that linkage chemistry may in some cases pick up additional binding interactions with the enzyme, thereby enhancing binding.

It should also be noted that the benefits of the α,α-disubstituted glycine ester motif described above (facile entry into the cell, carboxylesterase hydrolysis within the cell, and accumulation within the cell of active carboxylic acid hydrolysis product) are best achieved when the linkage between the amino add ester motif and the rest of the molecule is not a substrate for peptidase activity within the cell, which might result in cleavage of the amino acid from the molecule. Of course, stability to intracellular peptidases is easily tested by incubating the compound with disrupted cell contents, and analysing for any such cleavage.

For example, the α,α-disubstituted glycine ester (formula $H_2N—C(R_2R_3)—COOH$) may be conjugated to the modulator as (a) a radical of formula $—(CH_2)_z—X^1\text{-}L^1\text{-}Y—NH—C(R_2)(R_3)—R_1$ or (b) a radical of formula $—(CH_2)_z—Y^1\text{-}L^1\text{-}R_3—C(R_2)(NH_2)(R_1)$, wherein:

$R_1$ is the carboxylesterase-hydrolysable ester group;

$R_2$ and $R_3$ are the α-substituents of the α,α-disubstituted glycine;

$R_2$ is the side chain of a natural or non-natural alpha amino acid;

Y is a bond, —C(═O)—, $—S(═O)_2—$, —C(═O)O—, $—C(═O)NR_3—$, $—C(═S)—NR_4$, $—C(═NH)—NR_4$ or $—S(═O)_2NR_4—$ wherein $R_4$ is hydrogen or optionally substituted $C_1$-$C_6$ alkyl;

$Y^1$ is a bond, —C(═O)—, $—S(═O)_2—$, —C(═O)O—, —OC(═O)—, $—C(═O)NR_5—$, $—NR_5(C═O)—$, $—S(═O)_2NR_5—$, $—NR_5S(═O)_2—$, or $—NR_6(C═O)NR_5—$, wherein $R_5$ and R6 are independently hydrogen or optionally substituted $(C_1$-$C_6)$alkyl, $L^1$ is a divalent radical of formula $\text{-}(Alk^1)_m(Q)_n(Alk^2)_p\text{-}$ wherein m, n and p are independently 0 or 1, Q is (i) an optionally substituted divalent mono- or bicyclic, carbocyclic or heterocyclic radical having 5-13 ring members, or (I), in the case where p is 0, a divalent radical of formula $\text{-}Q^1\text{-}X^2—$ wherein $X^2$ is —O—, —S— or $NR^A—$ wherein $R^A$ is hydrogen or optionally substituted $C_1$-$C_3$ alkyl, and $Q^1$ is an optionally substituted divalent mono- or bicyclic carbocyclic or heterocyclic radical having 5-13 ring members, $Alk^1$ and $Alk^2$ independently represent optionally substituted divalent $C_3$-$C_7$ cycloalkyl radicals, or optionally substituted straight or branched, $C_1$-$C_6$ alkylene, $C_2$-$C_6$ alkenylene, or $C_2$-$C_8$ alkynylene radicals which may optionally contain or terminate in an ether (—O—), thioether (—S—) or amino $(—NR^A—)$ link wherein $R^A$ is hydrogen or optionally substituted $C_1$-$C_3$ alkyl;

$X^1$ is a bond, —C(═O)—; or $—S(═O)_2—$; $—NR_7C(═O)—$, $—C(═O)NR_7—$, $—NR_7C(═O)—NR_8—$, $—NR_7S(═O)_2—$, or $—S(═O)_2NR_7—$ wherein $R_7$ and $R_8$ are independently hydrogen or optionally substituted $C_1$-$C_6$ alkyl; and z is 0 or 1.

Taking the variables present in the linkage radical in turn:

z may be 0 or 1, so that a methylene radical linked to the modulator is optional.

specific preferred examples of Y include a bond, —(C═O)—, —(C═O)NH—, and —(C═O)O—. However, for hCE-1 specificity when the alpha amino acid ester is conjugated to the Inhibitor as a radical of formula (IA), Y should be a bond.

In the radical L, examples of $Alk^1$ and $Alk^2$ radicals, when present, include $—CH_2—$, $—CH_2CH_2—$ $—CH_2CH_2CH_2—$, $—CH_2CH_2CH_2CH_2—$, —CH═CH—, $—CH═CHCH_2—$, $—CH_2CH═CH—$, $CH_2CH═CHCH_2—$, —C≡C—, $—C≡CCH_2—$, $CH_2C≡C—$, and $CH_2C≡CCH_2$. Additional examples of $Alk^1$ and $Alk^2$ include $—CH_2W—$, $—CH_2CH_2W—$ $—CH_2CH_2WCH_2—$, $—CH_2CH_2WCH(CH_3)—$, $—CH_2WCH_2CH_2—$, $—CH_2WCH_2CH_2WCH_2—$, and $—WCH_2CH_2—$ where W is —O—, —S—, —NH—, $—N(CH_3)—$, or $—CH_2CH_2N(CH_2CH_2OH)CH_2—$. Further examples of $Alk^1$ and $Alk^2$ include divalent cyclopropyl, cyclopentyl and cyclohexyl radicals.

In $L^1$, when n is 0, the radical is a hydrocarbon chain (optionally substituted and perhaps having an ether, thioether or amino linkage). Presently it is preferred that there be no optional substituents in $L^1$. When both m and p are 0, $L^1$ is a divalent mono- or bicyclic carbocylic or heterocyclic radical with 5-13 ring atoms (optionally substituted). When n is 1 and at least one of m and p is 1, $L^1$ is a divalent radical including a hydrocarbon chain or chains and a mono- or bicyclic carbocyclic or heterocylic radical with 5-13 ring atoms (optionally substituted). When present, Q may be, for example, a divalent phenyl, naphthyl, cyclopropyl, cyclopentyl, or cyclohexyl radical, or a mono-, or bi-cyclic heterocyclic radical having 5 to 13 ring members, such as piperidinyl, piperazinyl, indolyl, pyridyl, thienyl, or pyrrolyl radical, but 1,4-phenylene is presently preferred.

Specifically, in some embodiments of the invention, m and p may be 0 with n being 1. In other embodiments, n and p may be 0 with m being 1. In further embodiments, m, n and p may be all 0. In still further embodiments m may be 0, n may be 1 with Q being a monocyclic heterocyclic radical, and p may be 0 or 1. $Alk^1$ and $Alk^2$, when present, may be selected from $—CH_2—$, $—CH_2CH_2—$, and $—CH_2CH_2CH_2—$ and Q may be 1,4-phenylene.

Modulators of Intracellular Enzymes and Receptors

The principles of this invention can be applied to modulators of a wide range of intracellular targets which are implicated in a wide range of diseases. As discussed, the binding modes of known modulators to their targets are generally known soon after the modulators themselves become known. In addition, modern techniques such as X-ray crystallography and NMR are capable of revealing such binding topologies and geometries, as are traditional medicinal chemistry methods of characterising structure-activity relationships. With such knowledge, it is straightforward to identify where in the structure of a given modulator an carboxylesterase ester motif could be attached without disrupting the binding of the modulator to the enzyme or receptor by use of structural data. For example, Table 1 lists some intracellular enzyme or receptor targets where there is published crystal structural data.

TABLE 1

| Target | Crystal Structure reference | Target Disease |
|---|---|---|
| CD45 | Nam et al., J Exp Med 201, 441 (2005) | Autoimmune disease |
| Lck | Zhu et al., Structure 7, 651 (1999) | Inflammation |

TABLE 1-continued

| Target | Crystal Structure reference | Target Disease |
| --- | --- | --- |
| ZAP-70 | Jin et al., J Biol Chem 279, 42818 (2004) | Autoimmune disease |
| PDE4 | Huai et al., Biochemistry 42, 13220 (2003) | Inflammation |
| PDE3 | Scapin et al., Biochemistry 43, 6091 (2004) | Asthma |
| IMPDH | Intchak et al., Cell 85, 921 (1996) | Psoriasis |
| p38 MAPK | Wang et al., Structure 6, 1117 (1998) | Inflammation |
| COX2 | Kiefer et al., J Biol Chem 278, 45763, (2003) | Inflammation |
| Adenosine Kinase | Schumacher et al., J Mol Biol 298, 875 (2000) | Inflammation |
| PLA2 | Chandra et al., Biochemistry B 10914 (2002) | Psoriasis |
| PLC | Essen et al., Biochemistry 36, 1704, (1997) | Rheumatoid arthritis |
| PLD | Leiros et al., J Mol Biol 339, 805 (2004) | Inflammation |
| iNOS | Rosenfeld et al., Biochemistry 41, 13915 (2002) | Inflammation |
| LTA4 hydrolase | Rudberg et al., J Biol Chem 279, 27376 (2004) | Inflammation |
| ICE | Okamato et al., Chem Pharm Bull 47, 11 (1999) | Rheumatoid arthritis |
| GSK3β | Bertrand et al., J Mol Biol 333, 393 (2003) | Rheumatoid arthritis |
| PKC | Xu et al., JBC 279, 50401 (2004) | Inflammation |
| PARP | Ruf et al., PNAS (USA) 93, 7481 (1996) | Proliferative disorders |
| MetAP2 | Sheppard et al Bioorg Med Chem Lett 14, 865 (2004) | Rheumatoid arthritis |
| Corticosteroid receptor | Bledsoe et al., Cell 110, 93 (2002) | Inflammation |
| PI3K | Walker et al., Mol Cell Biol 6, 909 (2000) | Proliferative disorders |
| Raf | Wan et al., Cell 116, 855 (2004) | Proliferative disorders |
| AKT/PKB | Yang et al., Nat Struct Biol 9, 940 (2002) | Proliferative disorders |
| HDAC | Finnin et al., Nature 401, 188 (1999) | Proliferative disorders |
| c-Abl | Nagar et al., Cancer Res 62, 4236 (2002) | Proliferative disorders |
| IGF-1R | Munshi et al., Acta Crystallogr Sect D 59, 1725 (2003) | Proliferative disorders |
| Thymidylate Synthetase | Stout et al., Structure 6, 839 (1998) | Proliferative disorders |
| Glycinamide Ribonucleotide Formyltransferase | Klein et al., J Mol Biol 249, 153 (1995) | Proliferative disorders |
| Purine Nucleoside Phosphorylase | Koelner et al., J Mol Biol 280, 153 (1998) | Proliferative disorders |
| Estrone Sulphatase | Hernandez-Guzman et al., J Biol Chem 278, 22989 (2003) | Proliferative disorders |
| EGF-RTK | Stamos et al., J Biol Chem 277, 46265 (2002) | Proliferative disorders |
| Src kinase | Lamers et al., J Mol Biol 285, 713 (1999) | Proliferative disorders |
| VEGFR2 | McTigue et al., Structure 7, 319 (19999) | Proliferative disorders |
| Superoxide Dismutase | Hough et al., J Mol Biol 287, 579 (1999) | Proliferative disorders |
| Ornithine Decarboxylase | Almrud et al., J Mol Biol 295, 7 (2000) | Proliferative disorders |
| Topoisomerase II | Classen et al., PNAS (USA) 100, 10629 (2003) | Proliferative disorders |
| Topoisomerase I | Stoker et al., PNAS (USA), 99, 15387 (2002) | Proliferative disorders |
| Androgen Receptor | Matias et al., J Biol Chem 275, 26164 (2000) | Proliferative disorders |
| JNK | Heo et al., EMBO J 23, 2185 (2004) | Proliferative disorders |

TABLE 1-continued

| Target | Crystal Structure reference | Target Disease |
| --- | --- | --- |
| Farnesyl Transferase | Curtin et al., Bioorg Med Chem Lett 13, 1367 (2003) | Proliferative disorders |
| CDK | Davis et al., Science 291, 134 (2001) | Proliferative disorders |
| Dihydrofolate Reductase | Gargaro et al., J Mol Biol 277, 119 (1998) | Proliferative disorders |
| Flt3 | Griffith et al., Mol Cell 13, 169 (2004) | Proliferative disorders |
| Carbonic Anhydrase | Stams et al., Protein Sci 7, 556 (1998) | Proliferative disorders |
| Thymidine Phosphorylase | Norman et al., Structure 12, 75 (2004) | Proliferative disorders |
| Dihydropyrimidine Dehydrogenase | Dobritzsch et al., JBC 277, 13155, (2002) | Proliferative disorders |
| Mannosidase α, | Van den Eisen et al., EMBO J 20, 3008 (2001) | Proliferative disorders |
| Peptidyl-prolyl isomerase (Pin1) | Ranganathan et al., Cell 89, 875 (1997) | Proliferative disorders |
| Retinoid X Receptor | Egea et al., EMBO J 19, 2592 (2000) | Proliferative disorders |
| β-Glucuronidase | Jain et al., Nat Struct Biol 3, 375 (1996) | Proliferative disorders |
| Glutathione Transferase | Oakley et al., J Mol Biol 291, 913 (1999) | Proliferative disorders |
| hsp90 | Jez et al., Chem Biol 10, 361 (2003) | Proliferative disorders |
| IMPDH | intchak et al., Cell 85, 921 (1996) | Proliferative disorders |
| Phospholipase A2 | Chandra et al., Biochemistry 41, 10914 (2002) | Proliferative disorders |
| Phospholipase C | Essen et al., Biochemistry 36, 1704, (1997) | Proliferative disorders |
| Phospholipase D | Leiros et al., J Mol Biol 339, 805 (2004) | Proliferative disorders |
| MetAP2 | Sheppard et al. Bioorg Med Chem Lett 14, 865 (2004) | Proliferative disorders |
| PTP-1B | Andersen et al., J Biol Chem 275, 7101 (2000) | Proliferative disorders |
| Aurora Kinase | Fancelli et al., in press | Proliferative disorders |
| PDK-1 | Komander et al., Biochem J 375, 255 (2003) | Proliferative disorders |
| HMGCoA reductase | Istvan and Deisenhofer Science 292, 1160 (2001) | Atheriosclerosis |
| Oxidosqualene cyclase | Lenhart et al., Chem Biol 9, 639 (2002) | Hyper-cholesterolaemia |
| Pyruvate dehydrogenase stimulator | Mattevi et al., Science 255, 1544 (1992) | Cardiovascular disease |
| Adenylate cyclase | Zhang et al., Nature 386, 247 (1997) | Cardiovascular disease |
| PPARγ agonist | Ebdurp et al., J Med Chem 46, 1306 (2003) | Diabetes |
| Alcohol dehydrogenase | Bahnson et al., PNAS USA 94, 12797 (1997) | Alcohol poisoning |
| Hormone sensitive lipase | Wei et al., Nat Struct Biol 6, 340 (1999) | Insulin resistant diabetes |
| Adenosine kinase | Mathews et al., Biochemistry 37, 15607 (1998) | Epilepsy |
| Aldose reductase | Urzhmsee al., Structure 5, 601 (1997) | Diabetes |
| Vitamin D3 receptor | Tocchini-Valentini et al., PNAS USA 98, 5491 (2001) | Osteoporosis |
| Protein tyrosine phosphatase | Andersen et al., J Biol Chem 275, 7101 (2000) | Diabetes |
| HIV Protease | Louis et al., Biochemistry 37, 2105 (1998) | HIV |
| HCV Polymerase | Bressanelli et al., PNAS USA 96, 13034 (1999) | Hepatitis C |
| Neuraminidase | Taylor et al., J Med Chem 41, 798 (1998) | Influenza |
| Reverse Transcriptase | Das et al., J Mol Biol 264, 1085 (1996) | HIV |
| CMV Protease | Khayat et al., Biochemistry 42, 885 (2003) | CMV infection |
| Thymidine Kinase | Champness et al., Proteins 32, 350 (1998) | Herpes infections |

TABLE 1-continued

| Target | Crystal Structure reference | Target Disease |
|---|---|---|
| HIV Integrase | Molteni et al., Acta Crystallogr Sect D 57, 536 (2001) | HIV |

For the purpose of illustration, reference is made to known inhibitors of 5 of the above intracellular targets, whose binding mode to the target is known. These examples illustrate how such structural data can be used to determine the appropriate positions for the attachment of the α,α-disubstituted glycine carboxylesterase ester motif. Schematics of the active sites are shown together with representative inhibitors. In general, positions remote from the binding interface between modulator and target, and therefore pointing away from the enzyme binding interface into solvent are suitable places for attachment of the carboxylesterase ester motif and these are indicated in the diagrams.

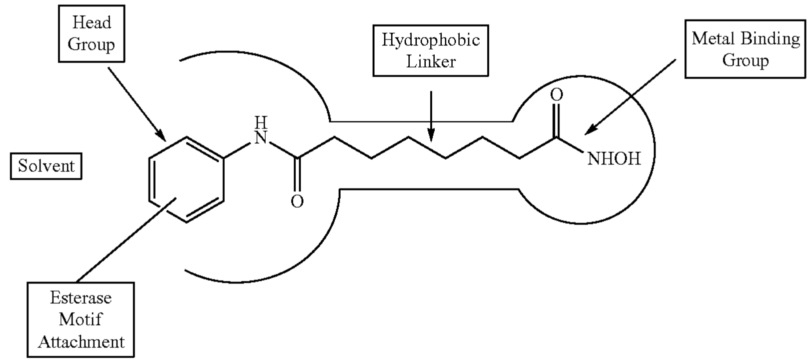

HDAC

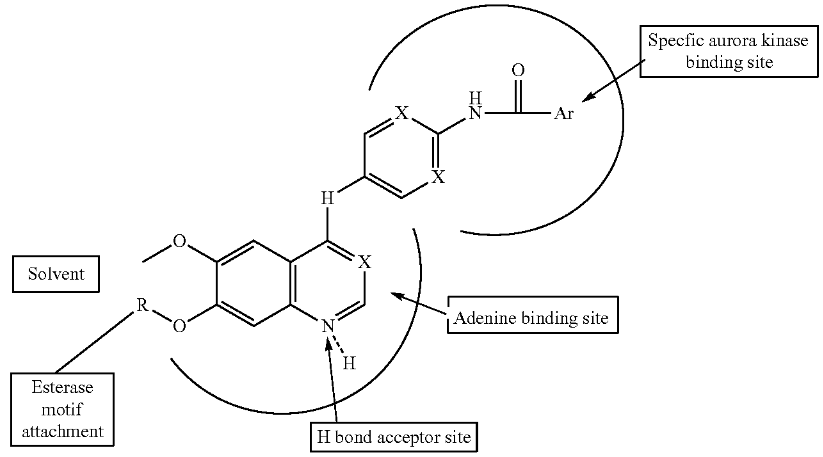

Aurora kinase

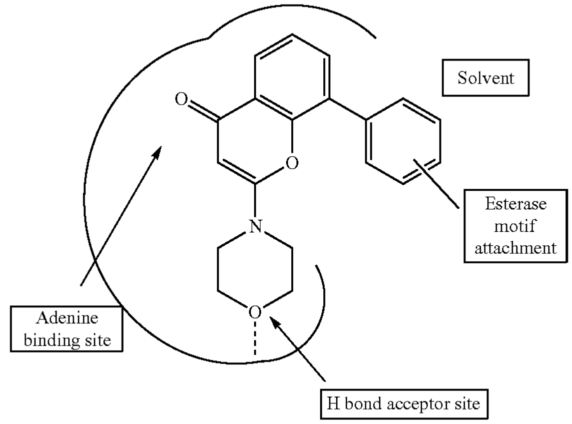

P13 Kinase

-continued

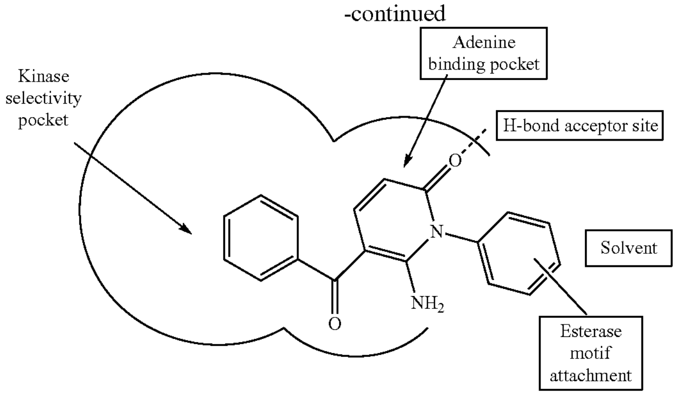

P38 MAP Kinase

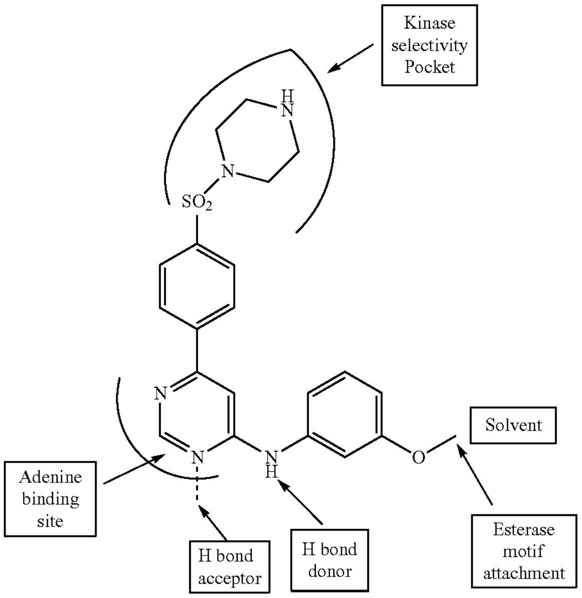

IKK kinase

A similar approach can also be used for the other examples identified in Table 1. The method of the invention, for increasing cellular potency and/or intracellular residence time of a modulator of the activity of a target intracellular enzyme or receptor, may involve several steps:

Step 1:

Identify a position or positions on one or a plurality of modulator molecules sharing the same binding mode for the target enzyme or receptor, remote from the binding interface between the modulators and the target enzyme or receptor.

Usually such positions are identified from the X-ray co-crystal structure (or structure derived by nmr) of the target enzyme or receptor with a known modulator (or a close structural analogue thereof) bound to the enzyme or receptor, by inspection of the structure. Alternatively the X-ray crystal structure of the target enzyme or receptor with the modulator docked into the active site of the enzyme or receptor is modelled by computer graphics methods, and the model is inspected The presumption is that structural modification of the modulator at positions remote from the binding interface is unlikely to interfere significantly with the binding of the modulator to the active site of the enzyme or receptor. Suitable positions will normally appear from the co-crystal structure or docked model to be orientated towards solvent.

Step 2:

Covalently modify the modulator(s) by attachment of an α,α-disubstituted glycine ester radical, or a range of different α,α-disubstituted glycine ester radicals at one or more of the positions identified in Step 1.

Attachment of α,α-disubstituted glycine ester radicals (ie the potential carboxylesterase motifs) may be via an existing covalent coupling functionality on the modulator(s), or via a suitable functionality specifically introduced for that purpose. The carboxylesterase motifs may be spaced from the main molecular bulk by a spacer or linker element, to position the motif deeper into solvent and thereby reduce still further any small effect of the motif on the binding mode of the modulator and/or to ensure that the motif is accessible to the carboxylesterase by reducing steric interference that may result from the main molecular bulk of the modulator.

Performance of Step 2 results in the preparation of one or, more usually, a small library of candidate modulators, each covalently modified relative to its parent inhibitor by the introduction of a variety of α,α-disubstituted glycine ester radicals, at one or more points of attachment identified in Step 1.

Step 3:

Test the α,α-disubstituted glycine ester-conjugated modulator(s) prepared in step 2 to determine their activity against the target enzyme or receptor.

As is normal in medicinal chemistry, the carboxylesterase motif version(s) of the parent modulator(s), prepared as a result of performing Steps 1 and 2, are preferably tested in assays appropriate to determine whether the expected retention of modulator activity has in fact been retained, and to what degree and with what potency profile. In accordance with the underlying purpose of the Invention, which is to cause the accumulation of modulator activity in cells, suitable assays will normally include assays in cell lines to assess degree of cellular activity, and potency profile, of the modified modulators. Other assays which may be employed in Step 3 include in vitro enzyme or receptor modulation assays to determine the intrinsic activity of the modified modulator and its putative carboxylesterase hydrolysis product; assays to determine the rate of conversion of the modified modulators to the corresponding carboxylic acid by carboxylesterases; and assays to determine the rate and or level of accumulation of the carboxylesterase hydrolysis product (the carboxylic acid) in cells. In such assays, both monocytic and non-monocytic cells, and/or a panel of isolated carboxylesterases, can be used in order to identify compounds that show cell selectivity.

If necessary or desirable, step 3 may be repeated with a different set of candidate alpha amino acid ester-conjugated versions of the parent modulator.

Step 4:

From data acquired in Step 3, select one or more of the tested α,α-disubstituted glycine ester-conjugated versions of the parent modulator(s) which cause modulation of enzyme or receptor activity inside cells, are converted to and accumulate as the corresponding carboxylic acid inside cells, and which show increased or prolonged cellular potency.

The above described Steps 1-4 represent a general algorithm for the implementation of the principles of the present invention.

Synthesis

There are multiple synthetic strategies for the synthesis of the compounds with which the present invention is concerned, but all rely on known chemistry, known to the synthetic organic chemist. Thus, compounds according to formula (I) can be synthesised according to procedures described in the standard literature and are well-known to those skilled in the art. Typical literature sources are "*Advanced organic chemistry*", $4^{th}$ Edition (Wiley), J March, "*Comprehensive Organic Transformation*", $2^{nd}$ Edition (Wiley), R. C. Larock, "*Handbook of Heterocyclic Chemistry*", $2^{nd}$ Edition (Pergamon), A. R. Katritzky), review articles such as found in "*Synthesis", "Acc. Chem. Res.", "Chem. Rev*", or primary literature sources identified by standard literature searches online or from secondary sources such as "*Chemical Abstracts*" or "*Belstein*".

The compounds of the invention may be prepared by a number of processes generally described below and more specifically in the Examples hereinafter. In the reactions described below, it may be necessary to protect reactive functional groups, for example hydroxyl, amino and carboxy groups, where these are desired in the final product, to avoid their unwanted participation in the reactions [see for example Greene, T. W., "Protecting Groups in Organic Synthesis", John Wiley and Sons, 1999]. Conventional protecting groups may be used in conjunction with standard practice. In some instances deprotection may be the final step in the synthesis of a compound of general formula (I), and the processes according to the invention described herein after are understood to extend to such removal of protecting groups.

The compounds of the invention may be prepared according to the following Examples. All temperatures are in ° C. The following abbreviations are used:

EtOAc=ethyl acetate
MeCN=acetonitrlle
MeOH=methanol
Boc=tert-butoxycarbonyl
CDI=1,1'-carbonyl diimidazole
DCM=dichloromethane
DBU=1,8-Diazabicyclo[5.4.0]undec-7-ene
DMAP=dimethylaminopyridine
DMF=dimethylformamide
DMSO=dimethyl sulfoxide
THF=tetrahydrofuran
HCl=hydrochloric acid
$NaHCO_3$=sodium hydrogen carbonate
TBDMSCl=tert-butyldimethylchlorosilane
NBS=N-bromosuccinimide
NMM=N-methyl morpholine
$NH_4Cl$=ammonium chloride
KHMDS=potassium bis(trimethylsilyl)amide
Pd/C=palladium on carbon
$MgSO_4$=magnesium sulfate
EDC=N-(3-Dimethylaminopropyl)-N'-ethylcarbodiimide hydrochloride
$Et_2O$=diethyl ether
$NaBH(OAc)_3$=sodium triacetoxyborohydride
HOBt=1-hydroxybenzotriazole
TFA=trifluoroacetic acid
TLC=thin layer chromatography
mL=milliliter(s)
g=gram(s)
mg=milligram(s)
mol=moles
mmol=millimole(s)
LCMS=high performance liquid chromatography/mass spectrometry
NMR=nuclear magnetic resonance
RT=room temperature Commercially available reagents and solvents (HPLC grade) were used without further purification. Solvents were removed using a Buchi rotary evaporator or a VirTis Benchtop SLC Freeze-dryer. Microwave irradiation was carried out using a Biotage Initiator™ Eight microwave synthesizer. Purification of compounds by flash chromatography column was performed using silica gel, particle size 40-63 μm (230-400 mesh) obtained from Fluorochem. Purification of compounds by preparative HPLC was performed on Gilson systems using reverse phase Axia™ prep Luna C18 columns (10 μm, 100×21.2 mm), gradient 0-100% B (A=water+0.05% TFA, B=acetonitrile) over 10 min, flow=25 mL/min, UV detection at 254 nm.

$^1H$ NMR spectra were recorded on a Bruker 300 MHz AV spectrometer in deuterated solvents. Chemical shifts δ are in parts per million. Thin-layer chromatography (TLC) analysis was performed with Kieselgel 60 $F_{254}$ (Merck) plates and visualized using UV light.

Analytical HPLC/MS was performed on an Agilent HP1100 LC system using reverse phase Luna C18 columns (3 μm, 50×4.6 mm), gradient 5-95% B (A=water+0.1% Formic acid, B=acetonitrile+0.1% Formic acid) over 2.25 min, flow=2.25 mL/min. UV spectra were recorded at 220 and 254 nm using a G1315B DAD detector. Mass spectra were obtained over the range m/z 150 to 800 on a LC/MSD SL G1956B detector. Data were integrated and reported using ChemStation and ChemStation Data Browser softwares.

Examples 1-6

The compounds 6-amino-5-(2,4-difluoro-benzoyl-1-phenyl-1H-pyridin-2-one (Compound I) and 6-amino-5-(2,4-difluoro-benzoyl-1-(2,5-difluorophenyl-1H-pyridin-2-one (Compound II):

Compound I

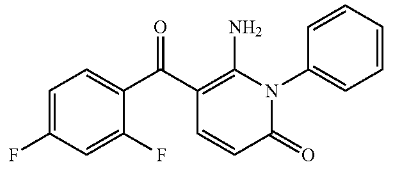

Compound II

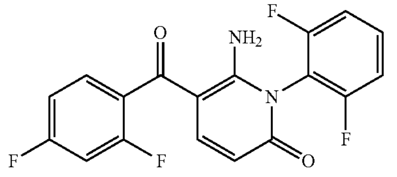

are known inhibitors of the intracellular enzyme p38 MAP kinase (WO 03/076405). Examples 1, 3 and 5 below relate to the covalent conjugation of esterase motifs with di-substitution at the alpha carbon of the amino acid ester to these compounds, in a position remote from the binding interface between the inhibitor and the target enzyme (see the comments above concerning the binding mode of a model p38 MAP kinase inhibitor). Examples 2, 4 and 6 below relate to the carboxylic acid esterase hydrolysis products of Examples 1, 3 and 5 respectively.

Synthesis of Examples 1-6

Intermediate 1: 4-Chlorophenyl 3-(2,4-difluorophenyl)-3-oxopropanimidothioate

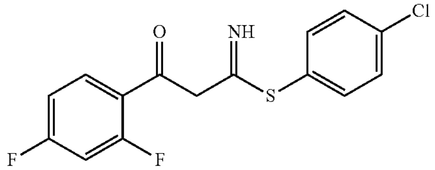 [SMILES: N=C(CC(=O)c1ccc(F)cc1F)Sc1ccc(Cl)cc1]

Intermediate 1 can be prepared using experimental procedures described in WO 2003076405.

Intermediate 2: {4-[6-Amino-5-(2,4-difluorobenzoyl)-2-oxopyridin-1(2H)yl]-phenyl}acetaldehyde

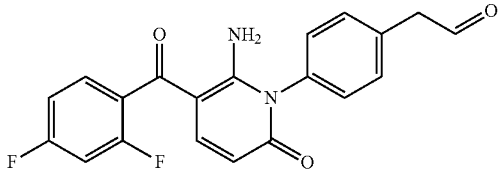 [SMILES: Nc1c(C(=O)c2ccc(F)cc2F)ccc(=O)n1-c1ccc(CC=O)cc1]

{4-[6-Amino-5-(2,4-difluorobenzoyl)-2-oxopyridin-1(2H)yl]-phenyl}acetaldehyde was synthesised using the mute shown in Scheme 1 below.

Scheme 1

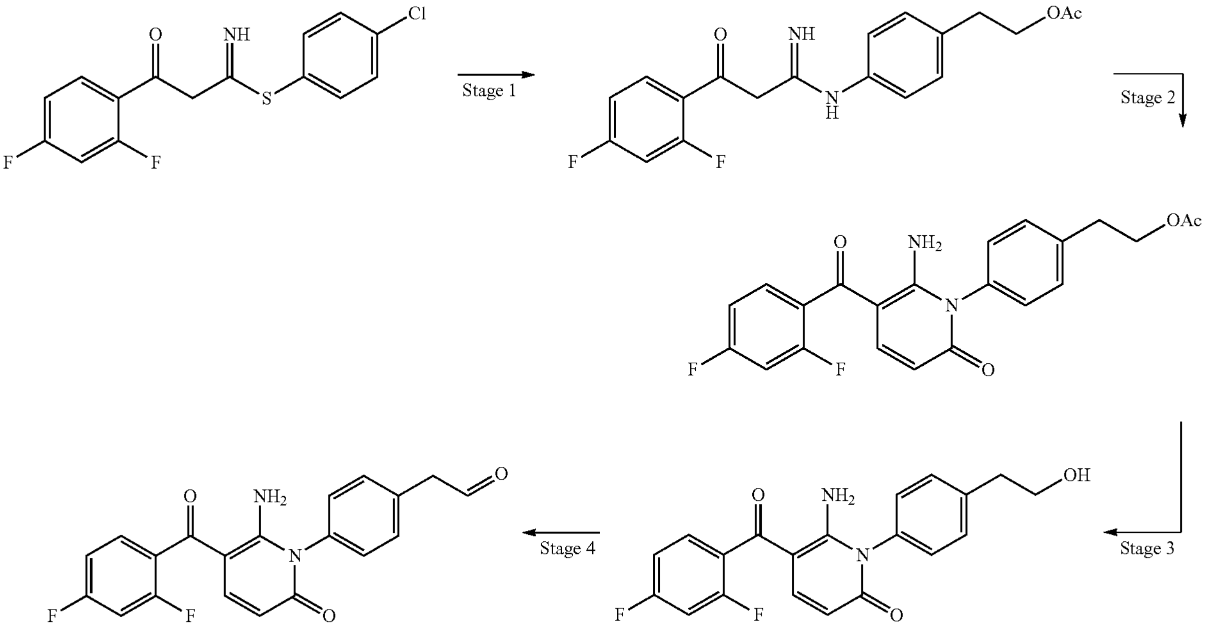

Stage 1—2-(4-{[3-(2,4-Difluorophenyl)-3-oxopropanimidoyl]amino}phenyl)ethyl acetate 4-Chlorophenyl 3-(2,4-difluorophenyl)-3-oxopropanimidothioate (Intermediate 1) (69.7 g, 192 mmol) was suspended in glacial acetic acid (700 mL) and 2-(4-aminophenyl)ethanol (27.71 g, 202 mmol, 1.05 eq) was added. The mixture was heated at 80° C. for 2.5 hours before being allowed to cool to room temperature and concentrated under reduced pressure. The residue was triturated with $Et_2O$ (500 mL) and washed with $Et_2O$ (2×250 mL) to give a white solid, which was suspended in saturated $NaHCO_3$ (700 mL) and stirred vigorously for 30 minutes. Filtration and washing with water afforded a beige solid which was dried under reduced pressure to give the title compound (64.12 g, 92% yield).

LC/MS: m/z 361 $[M+H]^+$. $^1H$ NMR (300 MHz, DMSO-$d_6$) δ: 7.79-7.71 (1H, m), 7.45-7.07 (6H, m), 5.26 (1H, s), 4.21 (2H, t, J=6.8 Hz), 2.89 (2H, t, J=6.5 Hz), 2.00 (3H, s).

Stage 2—2-{4-[6-Amino-5-(2,4-difluorobenzoyl)-2-oxopyridin-1(2H)-yl]phenyl}ethyl acetate CDI (43.26 g, 267 mmol, 1.5 eq) was dissolved in anhydrous THF (1 l) under an atmosphere of nitrogen and cooled to 0° C. Propiolic acid (16.43 mL, 267 mmol, 1.5 eq) was added dropwise and the mixture allowed to warm to room temperature and stirred for 1 hr. A suspension of 2-(4-{[3-(2,4-difluorophenyl)-3-oxopropanimidoyl]-amino}phenyl)ethyl acetate (64.12 g, 178 mmol) in anhydrous THF (500 mL) was added and the mixture heated at 80° C. for 6 hours before being left to stir at room temperature overnight. The resulting precipitate was collected by filtration, washed with $Et_2O$ and dried under reduced pressure to give the title compound as a pale yellow solid (39.56 g). The filtrate was concentrated under reduced pressure to give a brown oil that was triturated with EtOAc (500 mL), providing a second batch of product by filtration (7.21 g). The two batches were combined to afford the title compound as a yellow solid (46.77 g, 64% yield).

LC/MS: m/z 413 $[M+H]^+$. $^1H$ NMR (300 MHz, DMSO-$d_6$) δ: 7.55-7.37 (4H, m), 7.3-7.20 (4H, m), 5.72 (1H, d, J=9.6 Hz), 4.30 (2H, t, J=6.9 Hz), 3.01 (2H, t, J=6.9 Hz), 2.04 (3H, s).

Stage 3—6-Amino-5-(2,4-difluorobenzoyl)-1-[4-(2-hydroxyethyl)phenyl]pyridin-2(1H)-one 2-{4-[6-Amino-5-(2,4-difluorobenzoyl)-2-oxopyridin-1(2H)-yl]phenyl}ethyl acetate (46.77 g, 113 mmol) was suspended in 6N aqueous HCl (500 mL) and heated at reflux for 2 hours. A precipitate formed upon cooling to room temperature which was collected by filtration, suspended in saturated aqueous $NaHCO_3$ (1000 mL) and stirred vigorously for 30 minutes. Filtration, washing with water (2×500 mL) and drying under reduced pressure afforded the title compound as an off-white solid (40.11 g, 96% yield).

LC/MS: m/z 371 $[M+H]^+$. $^1H$ NMR (300 MHz, DMSO-$d_6$) δ: 7.55-7.37 (4H, m), 7.31-7.20 (4H, m), 5.71 (1H, d, J=9.9 Hz), 4.69 (1H, t, J=5.3 Hz), 3.71 (2H, m), 2.84 (2H, d, J=6.9 Hz).

Stage 4—{4-[6-Amino-5-(2,4-difluorobenzoyl)-2-oxopyridin-1(2H)-yl]phenyl}-acetaldehyde To a suspension of 6-amino-5-(2,4-difluorobenzoyl)-1-[4-(2-hydroxyethyl)phenyl]-pyridin-2(1H)-one (15.00 g, 40.5 mmol) in anhydrous DCM (750 mL) at 0° C. was added Dess-Martin Periodinane (20.62 g, 48.6 mmol, 1.2 eq) in portions. The mixture was allowed to warm to room temperature and stirred for 3 hours, before being poured into saturated aqueous $NaHCO_3$ (400 mL) and saturated aqueous $Na_2S_2O_3$ (400 mL) and stirred vigorously for 30 minutes. The aqueous layer was separated and extracted with DCM (2×500 mL), and the organic extracts combined and dried over $MgSO_4$. Filtration and concentration under reduced pressure afforded the title compound as a crude pale yellow solid that was used without further purification (15.13 g).

LC/MS: m/z 369 $[M+H]^+$.

Intermediate 3: Cyclopentyl 2-methylalaninate hydrochloride

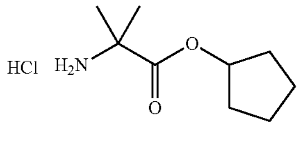

Intermediate 3 was synthesised using the route shown in Scheme 2 below.

Scheme 2

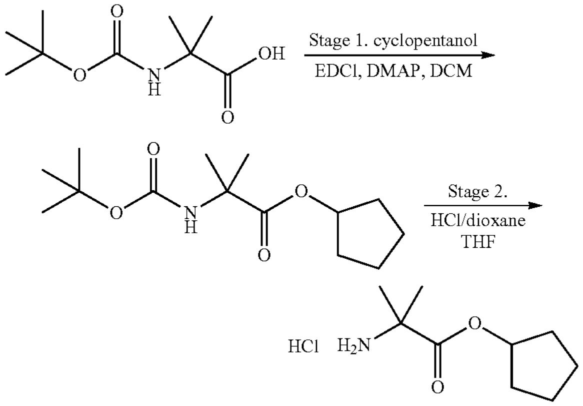

Stage 1—Cyclopentyl N-(tert-butoxycarbonyl)-2-methylalaninate

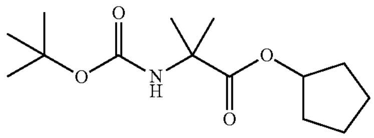 [SMILES: CC(C)(C)OC(=O)NC(C)(C)C(=O)OC1CCCC1]

To a solution of N-(tert-butoxycarbonyl)-2-methylalanine (1.00 g, 4.92 mmol) in DCM (10 mL) at 0° C. was added cyclopentanol (0.83 mL, 9.84 mmol), EDCl (1.06 g, 5.42 mmol) and finally DMAP (60 mg, 0.49 mmol). The reaction mixture was warmed to RT and stirred for 18 hours The DCM was removed in vacuo to give a clear oil. The crude residue was dissolved in EtOAc (100 mL) and washed with water, 1M $NaHCO_3$ and brine. The organic phase was dried ($MgSO_4$) and concentrated in vacuo. The crude extract was purified by column chromatography (10% EtOAc in heptane) to yield the desired product as a clear oil (0.254 g, 20% yield).

$^1H$ NMR (300 MHz, $CDCl_3$) δ: 5.25-5.17 (1H, m), 5.04 (1H, br s), 1.93-1.54 (8H, m), 1.49 (6H, s), 1.45 (9H, s).

Stage 2—Cyclopentyl 2-methylalaninate hydrochloride (Intermediate 3)

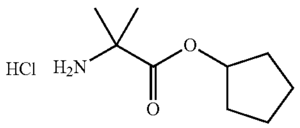

Cyclopentyl N-(tert-butoxycarbonyl)-2-methylalaninate (0.254 g, 0.93 mmol) was dissolved in THF (5 mL) and treated with 4M HCl/dioxane (2 mL) and the reaction mixture was stirred at RT for 24 hours. The crude mixture was concentrated under reduced pressure and triturated with $Et_2O$ to give a white precipitate. This was further washed with $Et_2O$ to give the desired product as a white powder (0.16 g, 82% yield).

$^1H$ NMR (300 MHz, DMSO-$d_6$) δ: 8.58 (3H, br s), 5.21-5.14 (1H, m), 1.93-1.78 (2H, m), 1.74-1.53 (6H, m), 1.45 (6H, s).

Intermediate 4: tert-Butyl 2-methylalaninate

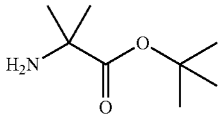

Intermediate 4 was synthesised using the route shown in Scheme 3 below.

Scheme 3

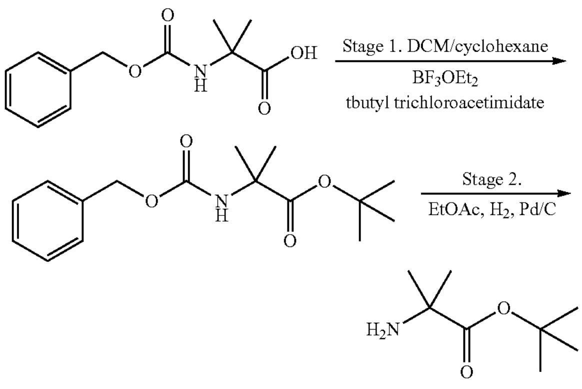

Stage 1—tert-Butyl N-[(benzyloxy)carbonyl]-2-methylalaninate

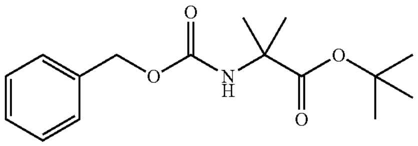 [SMILES: CC(C)(C)OC(=O)C(C)(C)NC(=O)OCc1ccccc1]

To a solution of N-[(benzyloxy)carbonyl]-2-methylalanine (1 g, 4.21 mmol) in DCM (10 mL anhydrous) and cyclohexane (10 mL) at 0° C. under nitrogen was added boron trifluoride diethyl etherate (7.7 ul, catalytic). tert-Butyl 2,2,2-trichloroacetimidate (1.51 mL, 8.43 mmol) in cyclohexane (10 mL) was then added slowly over 30 minutes before allowing to warm to RT. Reaction was allowed to stir at RT for 16 hours. To the crude reaction mixture was added 190 mg of $NaHCO_3$ and the reaction filtered. The mother liquors were concentrated in vacuo. The crude extract was purified by column chromatography (10% EtOAc in heptane) to yield the desired product (0.863 g, 70% yield).

$^1H$ NMR (300 MHz, $CDCl_3$) δ: 7.39-7.31 (5H, m), 5.46 (1H, br s), 5.10 (2H, s), 1.54 (6H, s), 1.45 (9H, s).

Stage 2—tert-butyl 2-methylalaninate (Intermediate 4)

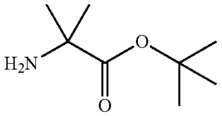

To a solution of tert-Butyl N-[(benzyloxy)carbonyl]-2-methylalaninate (0.863 mg, 2.90 mmol) in EtOAc (20 mL) was added 100 mg of Pd/C catalyst. The mixture was evacuated and stirred under an atmosphere of hydrogen for 18 hours, filtered (CELITE®), washed with EtOAc and concentrated in vacuo. The product was isolated as a yellow oil (0.45 mg, 96%) which contained traces of EtOAc. The product is believed to be volatile so caution is needed during evaporation in vacuo. $^1H$ NMR (300 MHz, $CDCl_3$) δ: 1.48 (9H, s), 1.32 (6H, s).

Intermediate 5: Cyclopentyl 1-aminocyclopentanecarboxylate

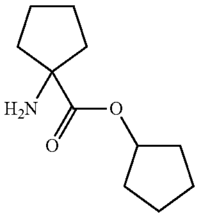 [SMILES: NC1(C(=O)OC2CCCC2)CCCC1]

Intermediate 5 was synthesised using the route shown in Scheme 4 below.

Scheme 4

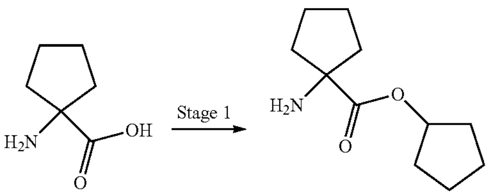

Intermediate 5

Stage 1—Cyclopentyl 1-aminocyclopentanecarboxylate

To a solution of 1-aminocyclopentanecarboxylic acid (2.58 g, 19.97 mmol) in cyclopentanol (20 mL), was added concentrated sulfuric acid (2.15 g, 21.97 mmol) and the mixture stirred overnight at 70° C. The reaction was allowed to cool to RT and the cyclopentanol removed under reduced pressure. The residue was dissolved in EtOAc (30 mL) and washed with sat. $NaHCO_3$ (30 mL) and water (3×20 mL) then dried ($MgSO_4$), filtered and concentrated in vacuo to leave a dark yellow oil. Purification by column chromatography (15% 1.2M $NH_3$/MeOH in EtOAc) afforded the desired product (1.97 g, 50% yield).

$^1$H NMR (300 MHz, $CDCl_3$) δ: 5.21-5.17 (1H, m), 2.15-1.90 (2H, m), 1.85-1.57 (14H, m).

Intermediate 6: tert-Butyl 1-aminocyclopentanecarboxylate

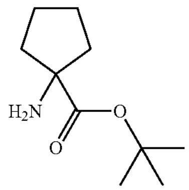

Intermediate 6 was synthesised using the route shown in Scheme 5 below.

Scheme 5

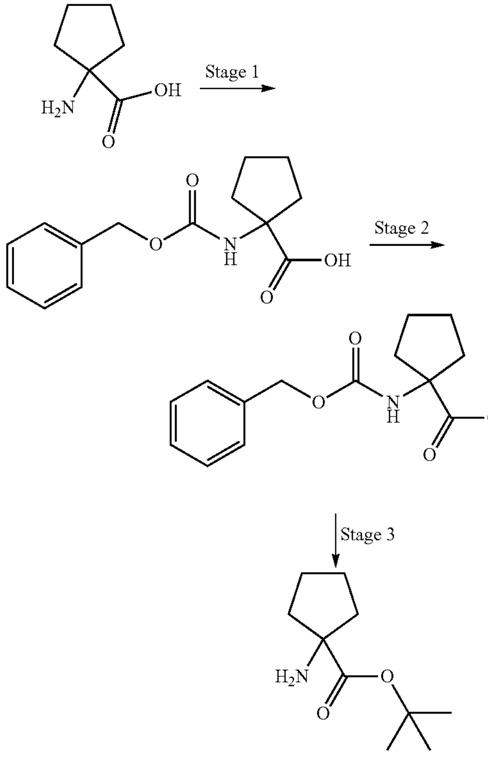

Intermediate 6

Stage 1—1-{[(Benzyloxy)carbonyl]amino}cyclopentanecarboxylic acid

To a solution of 1-aminocyclopentanecarboxylic acid (3.0 g, 23.2 mmol) in 1:1 dioxane/water (60 mL), was slowly added $Na_2CO_3$ (12.3 g, 116 mmol) followed by benzyl chloroformate (3.6 mL, 25.5 mmol) and the mixture stirred overnight at RT. The reaction mixture was carefully acidified to pH=2 with 1M HCl then extracted with EtOAc (3×30 mL). The combined organic extracts were washed with brine (30 mL), dried ($MgSO_4$), filtered and concentrated in vacuo to leave a pale yellow oil. LCMS and NMR showed the crude product to be a mixture of desired product and corresponding benzyl ester. The crude product was dissolved in 1:1 THF/water (60 mL) and treated with lithium hydroxide (2.67 g, 116 mmol). The mixture was stirred at RT overnight then washed with $Et_2O$ (3×30 mL), acidified to pH=2 and extracted with EtOAc (3×30 mL). The combined organic extracts were washed with brine (30 mL), dried ($MgSO_4$), filtered and concentrated under reduced pressure to afford the title compound (4.76 g, 78%). LCMS: m/z 264 $[M+H]^+$.

Stage 2—tert-Butyl 1-{[(benzyloxy)carbonyl]amino}cyclopentanecarboxylate tert-Butyl 1-{[(benzyloxy)carbonyl]amino}cyclopentanecarboxylate was prepared in a similar fashion to Stage 1 (Scheme 3) of Intermediate 4.

LC/MS: m/z 320 $[M+H]^+$.

Stage 3—tert-Butyl 1-aminocyclopentanecarboxylate tert-Butyl 1-aminocyclopentanecarboxylate was prepared in a similar fashion to Stage 2 (Scheme 3) of Intermediate 4.

$^1$H NMR (300 MHz, $CDCl_3$) δ: 2.08-2.02 (2H, m), 1.87-1.72 (4H, m), 1.64-1.58 (2H, m), 1.47 (9H, s).

Example 1

Cyclopentyl N-(2-{4-[6-amino-5-(2,4-difluorobenzoyl)-2-oxopyridin-1(2H)-yl]phenyl}-ethyl-2-methylalaninate

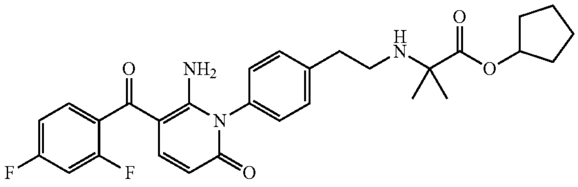 [SMILES: CC(C)(NCCc1ccc(-n2c(N)c(C(=O)c3ccc(F)cc3F)ccc2=O)cc1)C(=O)OC1CCCC1]

In this example compound of the invention, a dimethyl glycine cyclopentyl ester motif is covalently conjugated to the parent p38 MAP kinase inhibitor via the amino group of the dimethyl glycine cyclopentyl ester and through a $-CH_2CH_2-$ linker radical.

The compound was synthesised using Intermediate 2 and Intermediate 3 as described below.

To a solution of Intermediate 2 (189 mg, 0514 mmol) in anhydrous THF (4 mL) were added cyclopentyl 2-methylalaninate hydrochloride (Intermediate 3) (160 mg, 0.77 mmol, 1.5 eq) and $NaBH(OAc)_3$ (326 mg, 1.54 mmol, 3 eq). The mixture was stirred at room temperature for 16 hours, and then quenched with water (20 mL). The aqueous layer was extracted with EtOAc (3×20 mL), and the combined organic extracts washed with brine (40 mL), dried over $MgSO_4$, filtered and concentrated under reduced pressure. The residue was purified by preparative HPLC to provide the title compound (130 mg, 48% yield).

LC/MS: m/z 524 $[M+H]^+$. $^1H$ NMR (300 MHz, $CDCl_3$) δ: 10.43 (1H, br s), 7.51-7.34 (4H, m), 7.28-7.26 (2H, m), 7.04-6.90 (2H, m), 5.93 (1H, d, J=9.6 Hz), 5.20-5.10 (1H, m), 2.93-2.75 (4H, m), 1.95-1.55 (8H, m), 1.31 (6H, s).

Example 2

N-(2-{4-[6-Amino-5-(2,4-difluorobenzoyl)-2-oxopyridin-1 (2H-yl]phenyl}ethyl)-2-methylalanine

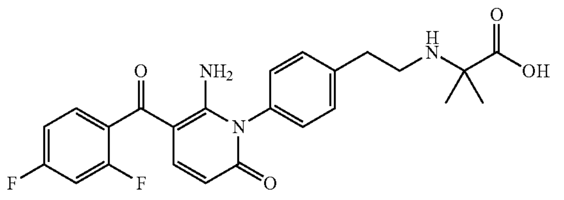 [SMILES: CC(C)(NCCc1ccc(-n2c(N)c(C(=O)c3ccc(F)cc3F)ccc2=O)cc1)C(=O)O]

This Example relates to the carboxylic acid hydrolysis product of the compound of Example 1.

The compound was synthesised using Intermediate 2 and Intermediate 4 as described below in Scheme 6.

Scheme 6

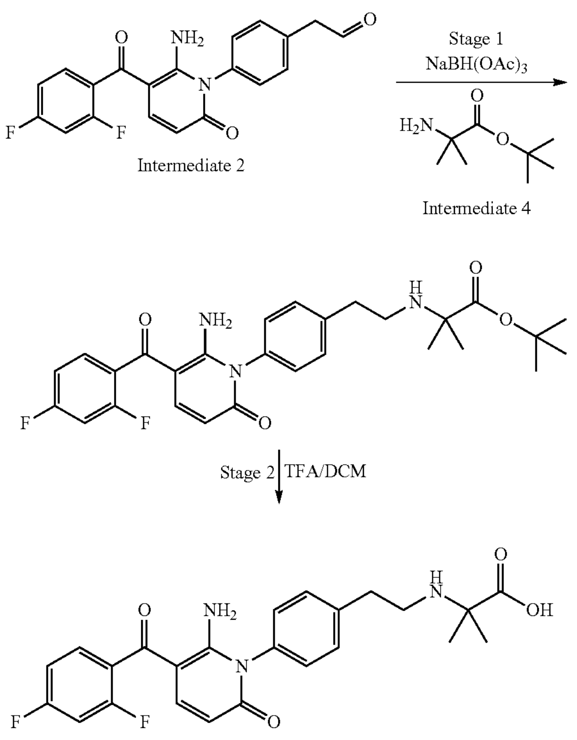

Stage 1—tert-Butyl N-(2-{4-[6-amino-5-(2,4-difluorobenzoyl)-2-oxopyridin-1(2H)-yl]phenyl}ethyl)-2-methylalaninate To a solution of Intermediate 2 (180 mg, 0.489 mmol) in THF (3 mL) was added tert-butyl 2-methylalaninate (Intermediate 4) (117 mg, 0.73 mmol), stirred for 30 minutes, and then $NaBH(OAc)_3$ (310 mg, 1.467 mmol). The reaction was stirred for 24 hours, diluted with EtOAc and the organic washed with sat $NaHCO_3$, brine, dried ($MgSO_4$) and concentrated in vacuo. The residue was purified by preparative HPLC to provide the title compound (120 mg, 48% yield).

LC/MS: m/z 512 $[M+H]^+$. $^1H$ NMR (300 MHz, $CDCl_3$) δ: 10.41 (1H, br s), 7.51-7.34 (4H, m), 7.28-7.26 (2H, m), 7.05-6.90 (2H, m), 5.93 (1H, d, J=9.9 Hz), 5.15 (1H, br s), 2.93-2.78 (4H, m), 1.46 (9H, s), 1.29 (6H, s).

Stage 2—N-(2-{4-[6-Amino-5-(2,4-difluorobenzoyl)-2-oxopyridin-(2H)-yl]phenyl})ethyl)-2-methylalanine To a solution of tert-Butyl N-(2-{4-[6-amino-5-(2,4-difluorobenzoyl)-2-oxopyridin-1(2H)-yl]phenyl}ethyl)-2-methylalaninate (100 mg, 0.19 mmol) In DCM (3 mL) was added trifluoroacetic acid (3 mL). The mixture was stirred at room temperature for 16 hours and concentrated under reduced pressure. The residue was triturated with $Et_2O$, collected by filtration and dried under reduced pressure to afford the title compound as an off-white solid (50 mg, 56% yield).

LC/MS: m/z 456 $[M+H]^+$. $^1H$ NMR (300 MHz, DMSO-$d_6$) δ: 10.05 (1H, br s), 7.60-7.15 (9H, m), 6.95 (1H, br s), 5.72 (1H, d, J=9.6 Hz), 3.15-2.95 (4H, m), 1.33 (6H, br s).

Example 3

Cyclopentyl 1-[(2-{4-[6-amino-5(2,4-difluorobenzoyl-2-oxopyridin-1(2H)-yl]phenyl}ethyl)amino] cyclopentanecarboxylate

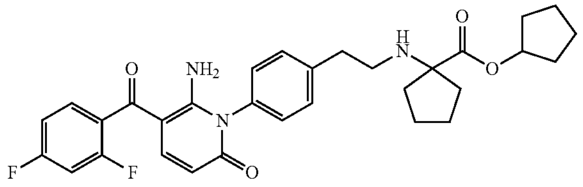 [SMILES: Nc1c(C(=O)c2ccc(F)cc2F)ccc(=O)n1-c1ccc(CCNC2(C(=O)OC3CCCC3)CCCC2)cc1]

Example 3 was synthesised using Intermediate 2 and Intermediate 5 in a similar manner to Example 1

LC/MS: m/z 550 $[M+H]^+$. $^1H$ NMR (300 MHz, DMSO-$d_6$) δ: 7.55-7.34 (6H, m), 7.29-7.21 (2H, m), 5.72 (1H, d, J=9.8 Hz), 5.27-5.21 (1H, m), 3.31-3.20 (2H, m), 3.10-3.00 (2H, m), 2.22-2.12 (2H, m), 2.08-1.98 (2H, m), 1.90-1.58 (12H, m)

Example 4

1-[(2-{4-[6-Amino-5-(2,4-difluorobenzoyl)-2-oxopyridin-1 (2H)-yl]phenyl}ethyl)amino]cyclopentanecarboxylic acid

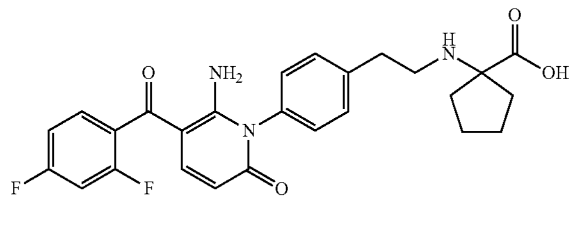 [SMILES: Nc1c(C(=O)c2ccc(F)cc2F)ccc(=O)n1-c1ccc(CCNC2(C(=O)O)CCCC2)cc1]

Example 4 was synthesized using Intermediate 2 and Intermediate 6 in a similar manner to Example 2.

LCMS: m/z 482 $[M+H]^+$. $^1H$ NMR (300 MHz, DMSO-$d_6$) δ: 7.52-7.37 (4H, m), 7.31-7.20 (4H, m), 5.71 (1H, d, J=10.0 Hz), 3.08-2.93 (4H, m), 2.10-1.99 (2H, m), 1.78-1.68 (6H, m).

Example 5

Cyclopentyl 5-{4-[6-amino-5(2,4-difluorobenzoyl-2-oxopyridin-1(2H)-yl]-3,5-difluorophenoxy}-2-methylnorvalinate

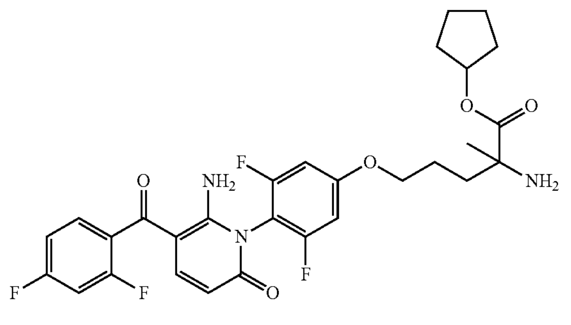 [SMILES: CC(N)(CCCOc1cc(F)c(-n2c(N)c(C(=O)c3ccc(F)cc3F)ccc2=O)c(F)c1)C(=O)OC1CCCC1]

$^1H$ NMR (300 MHz, DMSO-$d_6$) 10.14 (1H, br s), 8.06 (3H, br s), 7.57 (1H, dd, J=8.5, 15.1 Hz), 7.42 (1H, td, J=2.3, 10.0 Hz),), 7.34 (1H, dd, J=2.5, 9.8 Hz), 7.24 (1H, td, J=2.3, 8.5 Hz), 7.03 (2H, d, J=10.2 Hz) 5.74 (1H, d, J=9.8 Hz), 5.23-5.19 (1H, m), 4.13-4.07 (2H, m), 1.97-1.83 (5H, m), 1.70-1.57 (7H, m), 1.45 (3H, s). LCMS purity 95%, m/z 576 $[M+H]^+$.

Example 5 was synthesised by the route shown in Scheme 7.

Scheme 7

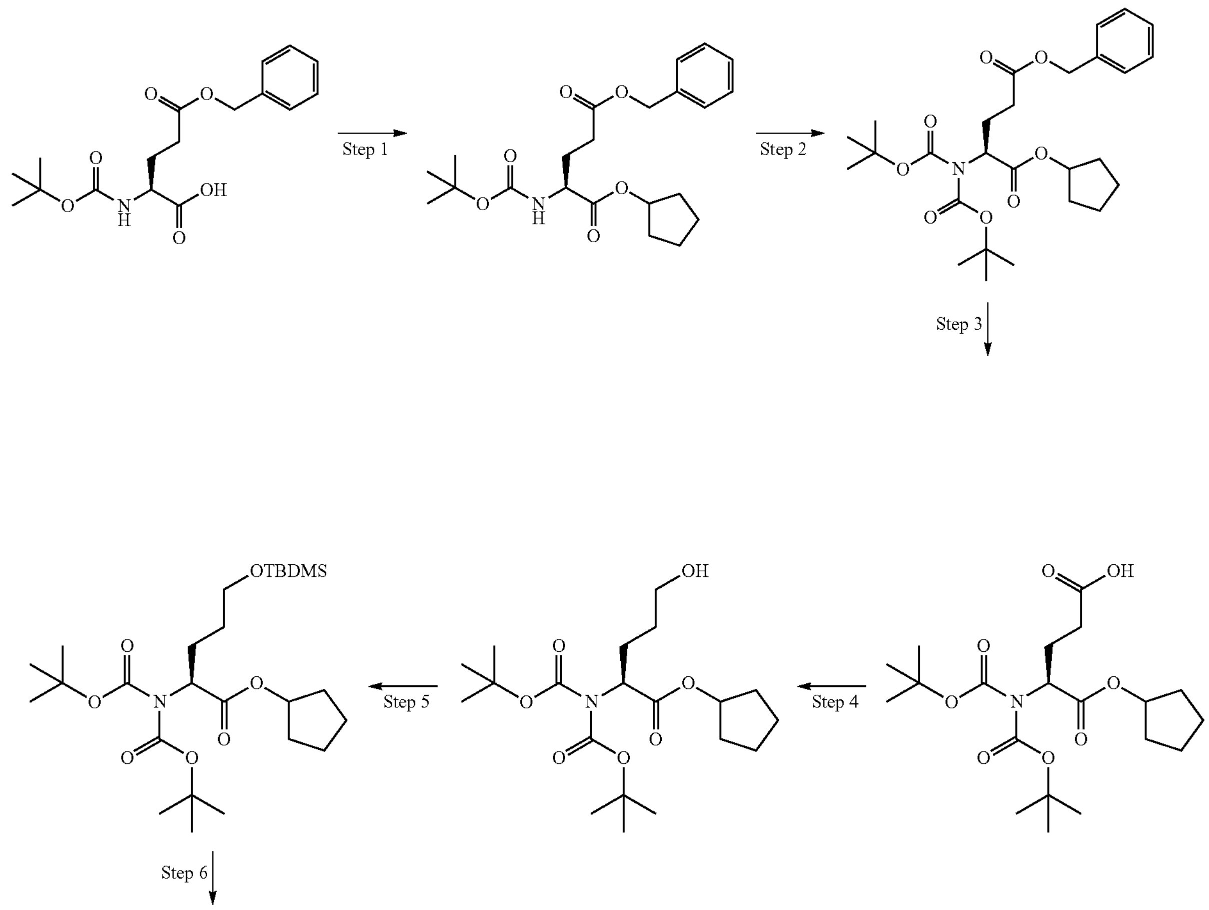

-continued

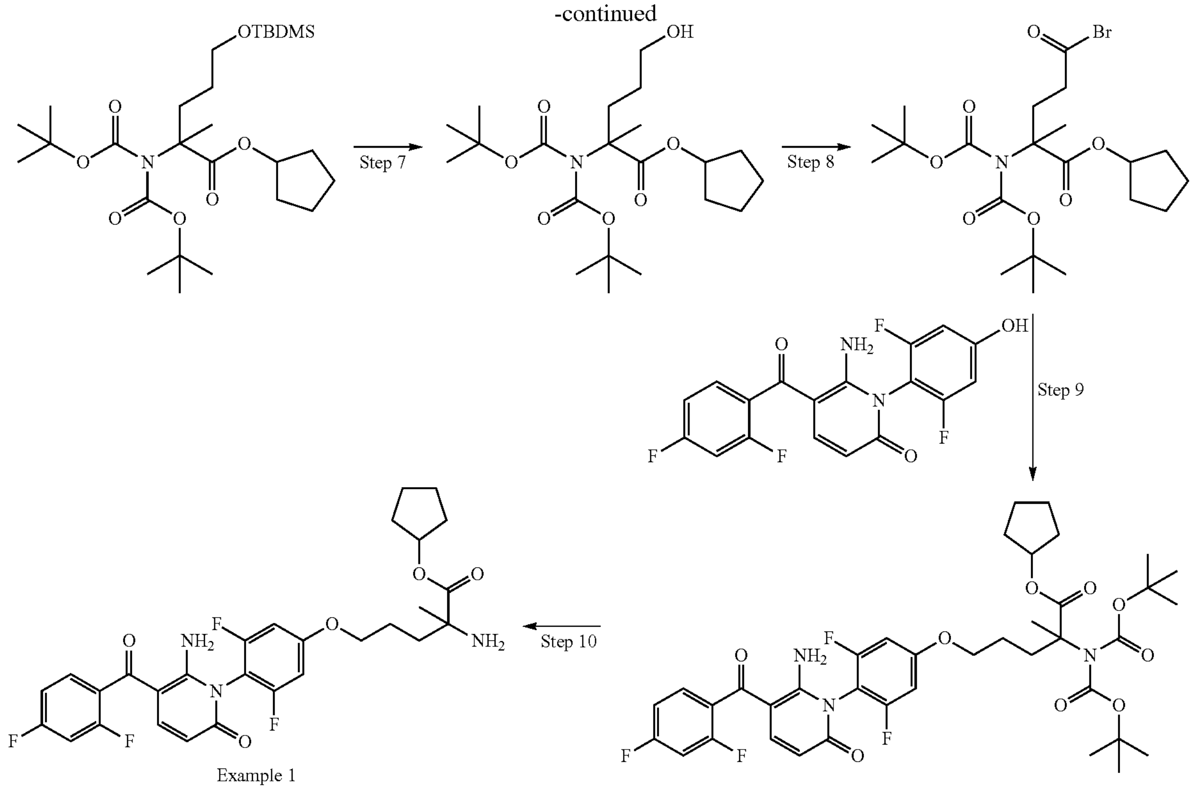

Example 1

Step 1: 5-Benzyl 1-cyclopentyl N-(tert-butoxycarbonyl)-L-glutamate

To a solution of (2S)-5-(benzyloxy)-2-[(tert-butoxycarbonyl)amino]-5-oxopentanoic acid (10 g, 30 mmol) in DCM (100 mL) was added cyclopentanol (30 mL, 33 mmol), EDC (6.25 g, 33 mmol) and DMAP (362 mg, 3 mmol). The reaction was allowed to stir for 20 hours for complete reaction. The reaction was diluted with DCM, washed with 1M HCl, sat $NaHCO_3$, brine, dried ($MgSO_4$) and concentrated in vacuo. The residue was purified by column chromatography (20% EtOAc/Heptane) to provide the title compound as a white solid (8.48 g, 71% yield). m/z 406 $[M+H]^+$.

Step 2: 5-Benzyl 1-cyclopentyl N,N-bis(tert-butoxycarbonyl)-L-glutamate

To a solution of 5-benzyl 1-cyclopentyl N-(tert-butoxycarbonyl)-L-glutamate (8.48 g, 21 mmol) in acetonitrile (100 mL) was added di-tert-butyl dicarbonate (13.69 g, 63 mmol) and DMAP (255 mg, 2.1 mmol). The reaction was heated to 50° C. and stirred overnight before being allowed to cool to room temperature and concentrated under reduced pressure. The crude residue was dissolved in EtOAc and washed with 1M HCl, sat $NaHCO_3$, and brine. The organic layer was dried over magnesium sulfate and concentrated in vacuo to give a brown oil. Purification by column chromatography (10-20% EtOAc/Heptane) provided the title compound as a colourless oil (10.16 g, 96% yield). m/z 506 $[M+H]^+$.

Step 3: (4S) 4-[Bis(tert-butoxycarbonyl)amino]-5-(cycopentyloxy)-5-oxopentanoic acid To a solution of 5-benzyl 1-cyclopentyl N,N-bis(tert-butoxycarbonyl)-L-glutamate (10.16 g, 20.1 mmol) in EtOAc (200 mL) was added Pd/C (1 g). The mixture was stirred under an atmosphere of $H_2$ for 19 hours, filtered through CELITE® and concentrated in vacuo to provide the title compound as a pale yellow oil (8.28 g, 99% yield), m/z 416 $[M+H]^+$.

Step 4: Cyclopentyl N,N-bis(tert-butoxycarbonyl)-5-hydroxy-L-norvalinate (4S)-4-[Bis(tert-butoxycarbonyl)amino]-5-(cyclopentyloxy)-5-oxopentanoic acid (8.28 g, 20 mmol) was dissolved in THF (80 mL) and cooled in an ice bath. NMM (3.3 mL, 30 mmol) was added followed by dropwise addition of isobutylchloroformate (3.6 mL, 28 mmol). The reaction was stirred at 0° C. for 1.5 hours before the reaction was filtered and the precipitate washed with THF. The mother liquors were cooled again to 0° C. and $NaBH_4$ (1.51 g, 40 mmol) added portionwise, stirring for 3 hours. The reaction mixture was quenched with water (80 mL) and extracted with EtOAc (3×100 mL). The combined organic extracts were washed with brine, dried ($MgSO_4$) and concentrated in vacuo to give a yellow oil. Purification by column chromatography (40% EtOAc/Heptane) provided the title compound as a colourless oil (4.34 g, 54% yield). m/z 402 $[M+H]^+$.

Step 5: Cyclopentyl N,N-bis(tert-butoxycarbonyl)-5-{[tert-butyl(dimethyl)silyl]oxy}-L-norvalinate Cyclopentyl N,N-bis(tert-butoxycarbonyl)-5-hydroxy-L-norvalinate (4.34 g, 10.8 mmol) was dissolved in acetonitrile (45 mL) and cooled in an ice bath. DBU (1.7 mL, 11.3 mmol) was added followed by TBDMSCl (1.71 g, 11.3 mmol). The reaction was allowed to stir overnight at room temperature and then concentrated in vacuo. The crude residue was dissolved in EtOAc and washed with 1M HCl, sat $NaHCO_3$, and brine. The organic layer was dried over magnesium sulfate and concentrated in vacuo to give a yellow oil. Purification by column chromatography (20% EtOAc/Heptane) provided the title compound as a colourless oil (3.82 g, 69% yield). m/z 516 $[M+H]^+$.

Step 6: Cyclopentyl N,N-bis(tert-butoxycarbonyl)-5-{[tert-butyl(dimethyl)silyl]oxy}-2-methylnorvalinate To a solution of cyclopentyl N,N-bis(tert-butoxycarbonyl)-5-{[tert-butyl(dimethyl)silyl]oxy}-L-norvalinate (3.82 g, 7.4 mmol) in THF (50 mL) at −78° C. under a $N_2$ atmosphere was added 0.91M KHMDS in THF (16.3 mL, 14.8 mmol). The reaction mixture was stirred at −78° C. for 1 hour before addition of methyl iodide (0.92 mL, 14.8 mmol). The reaction was allowed to warm to room temperature and stirred overnight. The reaction mixture was quenched with sat $NH_4Cl$ and the aqueous layer extracted with EtOAc (2×50 mL). The combined organic extracts were washed with brine, dried ($MgSO_4$) and concentrated in vacuo to give a yellow oil which was used without further purification (3.50 g, 89% yield). m/z 530 $[M+H]^+$.

Step 7: Cyclopentyl N,N-bis(tert-butoxycarbonyl)-5-hydroxy-2-methylnorvalinate

Cyclopentyl N,N-bis(tert-butoxycarbonyl)-5-{[tert-butyl(dimethyl)silyl]oxy}-2-methylnorvalinate was dissolved in acetic acid (45 mL), THF (15 mL) and water (15 mL). The reaction was allowed to stir at 30° C. for 20 hours for complete reaction. The reaction mixture was then diluted with EtOAc and washed with sat $NaHCO_3$ and brine. The organic layer was dried over magnesium sulfate and concentrated in vacuo to give a thick yellow oil which was taken forward without further purification (3.08 g). m/z 416 $[M+H]^+$.

Step 8: Cyclopentyl 5-bromo-N,N-bis(tert-butoxycarbonyl)-2-methylnorvalinate

NBS (3.95 g, 22.2 mmol) was suspended in DCM (30 mL) and triphenylphosphine added (5.44 g, 20.7 mmol). The reaction was stirred for 5 minutes before the addition of pyridine (0.94 mL, 8.9 mmol). Cyclopentyl N,N-bis(tert-butoxycarbonyl)-5-hydroxy-2-methylnorvalinate (3.08 g, 7.4 mmol) was then added as a solution in DCM (30 mL) and stirred overnight at room temperature. The reaction mixture was concentrated in vacuo to give a brown oil which was purified by column chromatography (15% EtOAc/Heptane) to provide the title compound as a colourless oil (1.05 g, 30% yield over two steps). m/z 479 $[M+H]^+$.

Step 9: Cyclopentyl 5-{4-[6-amino-5-(2,4-difluorobenzoyl)-2-oxopyridin-1(2H)-yl]-3,5-difluorophenoxy}-N,N-bis(tert-butoxycarbonyl)-2-methylnorvalinate 6-Amino-5-(2,4-difluorobenzoyl)-1-(2,6-difluoro-4-hydroxyphenyl)pyridin-2(1H)-one [Example 51 WO 03076405](500 mg, 1.32 mmol) and cyclopentyl 5-bromo-N,N-bis(tert-butoxycarbonyl)-2-methylnorvalinate (696 mg, 1.45 mmol) were mixed together in DMF (10 mL). Potassium carbonate (365 mg, 2.64 mmol) and sodium iodide (396 mg, 2.64 mmol) were then added, stirring at 40° C. overnight. The reaction mixture was then diluted with EtOAc (50 mL) and washed with water and brine. The organic layer was dried over magnesium sulfate and concentrated in vacuo to give a yellow solid which was purified by column chromatography (30-40% EtOAc/Heptane) to provide the title compound as a white solid (604 mg, 59% yield). m/z 776 $[M+H]^+$.

Step 10: Cyclopentyl 5-{4-[6-amino-5-(2,4-difluorobenzoyl)-2-oxopyridin-1(2H)-yl]-3,5-difluorophenoxy}-2-methylnorvalinate Cyclopentyl 5-{4-[6-amino-5-(2,4-difluorobenzoyl)-2-oxopyridin-1(2H)-yl]-3,5-difluorophenoxy}-N,N-bis(tert-butoxycarbonyl)-2-methylnorvalinate (604 mg) was dissolved in TFA (10 mL) and DCM (10 mL). The reaction was stirred at room temperature overnight. The reaction mixture was concentrated in vacuo to give a brown oil. The crude residue was then diluted with EtOAc (50 mL) and washed with sat $NaHCO_3$, water and brine. The organic layer was dried over magnesium sulfate and concentrated in vacuo to give a pale yellow solid Example 5 (387 mg, 48% yield).

Example 6

5-{4-[6-Amino-5-(2,4-difluorobenzoyl)-2-oxopyridin-1(2H)-yl]-3,5-difluorophenoxy}-2-methylnorvaline

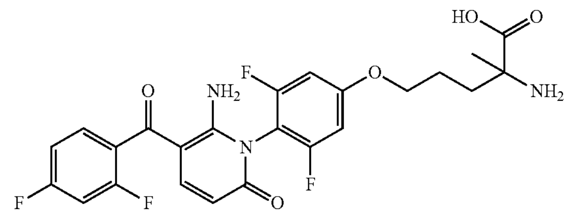 [SMILES: CC(N)(CCCOc1cc(F)c(-n2c(N)c(C(=O)c3ccc(F)cc3F)ccc2=O)c(F)c1)C(=O)O]

$^1H$ NMR (300 MHz, DMSO-$d_6$) 10.16 (1H, br s), 8.17 (3H, br s), 7.63-7.51 (1H, m), 7.47-7.18 (3H, m), 7.14-6.99 (2H, m), 6.23 (1H, d, J=9.6 Hz), 4.10 (2H, br s), 1.96-1.63 (4H, m), 1.41 (3H, s). LCMS purity 95%, m/z 508 $[M+H]^+$.

Example 6 was synthesised by the route shown in Scheme 8.

Scheme 8

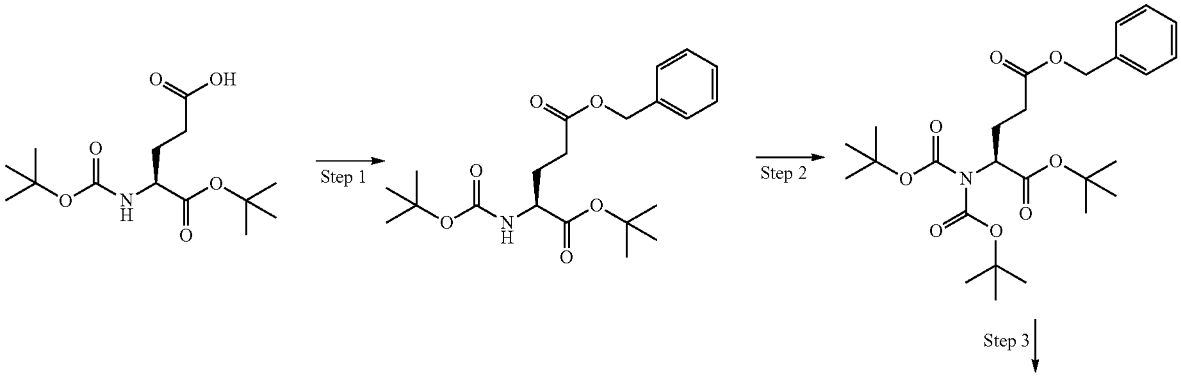

-continued

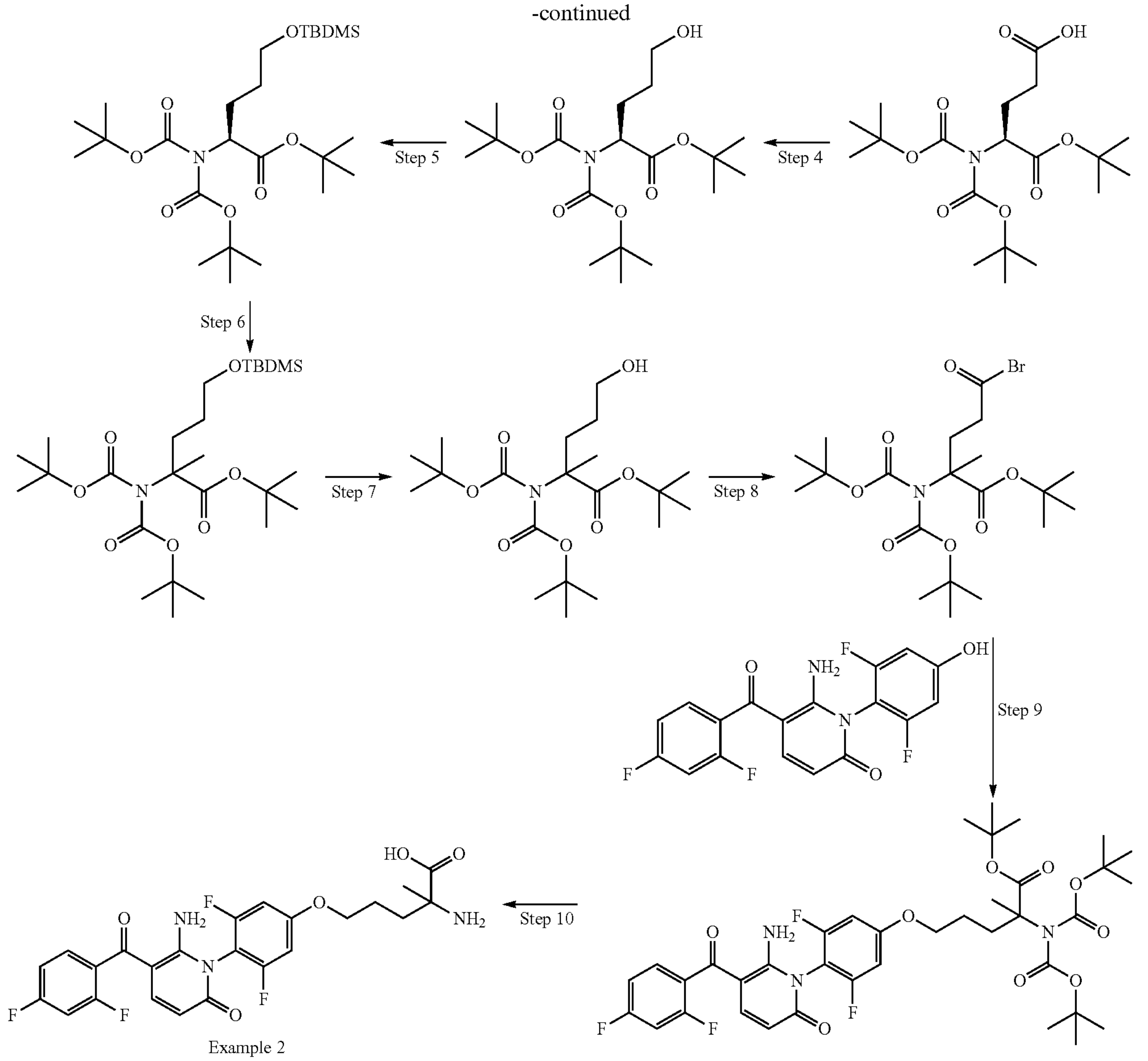

Example 2

Step 1: 5-Benzyl 1-tert-butyl N-(tert-butoxycarbonyl)-L-glutamate

To a solution of N-α-tert-butyloxycarbonyl-L-glutamic acid-α-tert-butyl ester (5 g, 16.5 mmol) in DCM (50 mL) was added benzyl alcohol (3.4 mL, 33 mmol), EDC 1M HCl, sat $NaHCO_8$, brine, dried ($MgSO_4$) and concentrated in vacuo. The residue 1M HCl, sat $NaHCO_3$, brine, dried ($MgSO_4$) and concentrated in vacuo. The residue was purified by column chromatography (20% EtOAc/Heptane) to provide the title compound as a colourless oil (5.98 g, 92% yield). m/z 416 $[M+Na]^+$.

Steps 2—9 follows the same methodology as described in Example 5 (Scheme 7).

Step 10: 5-{4-[6-Amino-5-(2,4-difluorobenzoyl)-2-oxopyridin-1(2H)-yl]-3,5-difluorophenoxy}-2-methylnorvaline tert-Butyl 5-{4-[6-amino-5-(2,4-difluorobenzoyl)-2-oxopyridin-1(2H)-yl]-3,5-difluorophenoxy}-N,N-bis(tert-butoxycarbonyl)-2-methylnorvalinate (70 mg) was dissolved in TFA (2 mL) and DCM (2 mL). The reaction was stirred at room temperature overnight. The reaction mixture was concentrated in vacuo to give a pink oil. The crude residue was then triturated with diethyl ether to give an off-white solid (23 mg, 40% yield) which was filtered off and dried under vacuum to give Example 6 as a TFA salt.

Compound IV (N-Hydroxy-3-phenyl-propionamide)

Compound IV

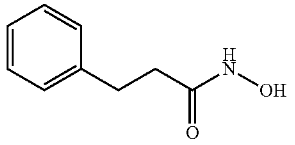

Compound IV was prepared as shown in Scheme 9 below

Scheme 9

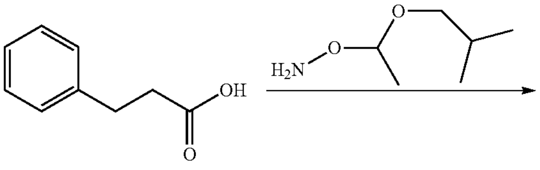

-continued

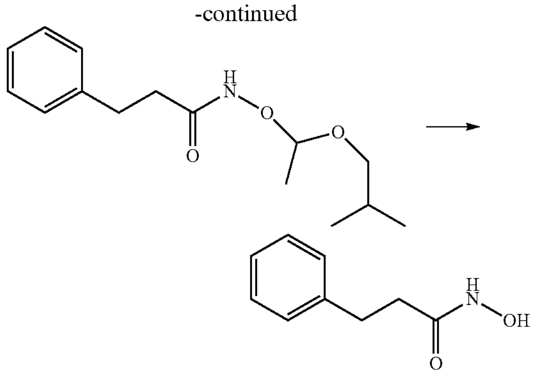

N-(1-isobutoxyethoxy)-3-phenylpropionamide

N-(3-Dimethylaminopropyl)-N'-ethylcarbodiimide hydrochloride (EDC) (151 mg) and 4-Dimethylaminopyridine (catalytic) were added to a stirred solution of hydrocinnamic acid (100 mg), protected hydroxylamine (WO2008/040934) (136 μL) and dichloromethane (5 mL) at RT under a nitrogen atmosphere. The reaction was stirred for 2 hours and then poured into water (50 mL). This was extracted with dichloromethane (2×50 mL). The combined organic layers were dried over sodium sulfate and solvent removed in vacuo. The residue was purified by column chromatography using an eluent of 0 to 100% ethyl acetate in heptanes, reached via a gradient to give the product as a colourless oil (58 mg).

Compound IV: N-Hydroxy-3-phenylpropionamide

N-(1-isobutoxyethoxy)-3-phenylpropionamide (58 mg) was dissolved in DCM (2 mL) and MeOH (0.5 mL) and stirred at RT under a nitrogen atmosphere. 4M HCl in dioxane (275 μL) was added to the solution and the reaction stirred for 2 hours. Solvent was then removed in vacuo and the residue purified by HPLC to give the product as a pink solid (9 mg).

m/z 166 $[M+H]^+$. $^1H$ NMR (300 MHz, DMSO-$d_6$) 10.37 (1H, bs), 7.21 (5H, m), 2.81 (2H, t, J=7.5 Hz), 2.61 (1H, m), 2.58 (2H, t, J=7.5 Hz).

Synthesis of Examples 7, 8, 9 and 10

The above compounds were synthesised using the intermediates and methods described below.

Intermediates

Intermediate 7: (2E)-3-(5-Formylpyridin-2-yl)-N-(1-isobutoxyethoxy) acrylamide

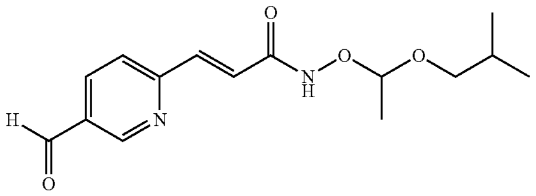 [SMILES: CC(C)COC(C)ONC(=O)/C=C/c1ccc(C=O)cn1]

Intermediate 7 was prepared by methods described in WO2008/040934.

Intermediate 8: 3-(4-formylphenyl)-N-(1-isobutoxyethoxy)propanamide

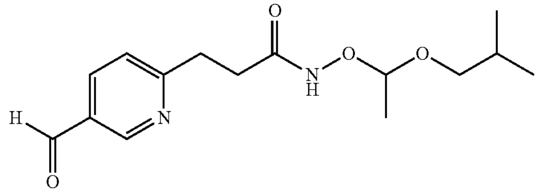 [SMILES: CC(C)COC(C)ONC(=O)CCc1ccc(C=O)cn1]

Intermediate 8 was prepared by methods described in WO2008/040934.

Intermediate 9: Cyclopentyl 1-aminocyclohexanecarboxylate

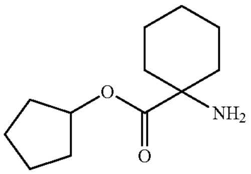 [SMILES: NC1(C(=O)OC2CCCC2)CCCCC1]

To 1-aminocyclohexanecarboxylic acid (4.2 g, 29 mmol) in cyclohexane (250 mL) was added cyclopentanol (50 mL) and para-toluenesulphonic acid (5.89 g) and the resulting suspension heated at reflux in a Dean-Stark apparatus for 72 hours. On cooling to room temperature the resulting white solid was collected by filtration and washed with cyclohexane (2×100 mL) and dried under reduced pressure to give the title compound (4.1 g) as a colourless solid. m/z 212.3 $[M+H]^+$.

Intermediate 10: Cyclopentyl 2-methyl-D,L-leucinate

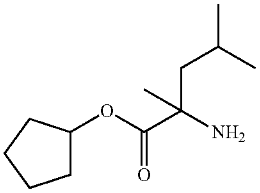

A solution of (R,S)-α-methylleucine (500 mg, 3.44 mmol) in cyclopentanol (1 mL) and conc. $H_2SO_4$ (0.36 mL) was heated at 80° C. for 28 hours. The reaction was concentrated under reduced pressure and the residue partitioned between saturated $NaHCO_3$ (aq) (20 mL) and dichloromethane (20 mL). The organic layer was dried ($MgSO_4$) and evaporated to give the desired material (650 mg) as a light brown oil which was used without further purification. m/z 214.3 $[M+H]^+$.

Examples

Example 7

Cyclopentyl 1-({4-[3-(hydroxyamino)-3-oxopropyl]benzyl}amino)cyclopentanecarboxylate

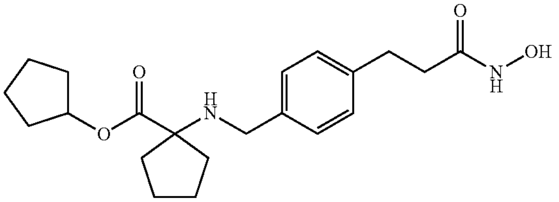 [SMILES: O=C(CCc1ccc(CNC2(C(=O)OC3CCCC3)CCCC2)cc1)NO]

To a solution of Intermediate 8 (208 mg, 0.68 mmol) and Intermediate 5 (184 mg, 0.68 mmol) in dichloromethane (20 mL) was added sodium triacetoxyborohydride (430 mg, 2.04 mmol) and acetic acid (47 μL). The resulting solution was stirred at room temperature for 5 hours and then quenched with saturated $NH_4C$. The reaction was extracted with dichloromethane (2×50 mL) and the combined organic layers were dried ($MgSO_4$) and concentrated in vacuo. The resulting residue was dissolved in 4M HCl in dioxane (1 mL) and stirred at room temperature for 1 hour. The reaction was quenched with $NaHCO_3$ and extracted with ethyl acetate (2×150 mL). The combined organic layers were dried ($MgSO_4$) and evaporated. The residue was purified by HPLC to give the title compound (80 mg) as a colourless solid. m/z 375 $[M+H]^+$. $^1H$ NMR (300 MHz, MeOD), 7.46 (2H, d J=7.9 Hz), 7.36 (2H, d J=8.1 Hz), 5.40 (1H, m), 4.18 (2H, s), 2.98 (2H, t, J=7.2 Hz), 2.38 (4H, m), 2.08-1.52 (14H, m).

Example 8

1-({4-[3-(Hydroxyamino-3-oxopropyl]benzyl}amino)cyclo pentanecarboxylic acid

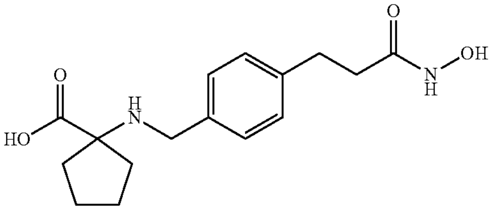 [SMILES: O=C(CCc1ccc(CNC2(C(=O)O)CCCC2)cc1)NO]

Cyclopentyl 1-({4-[3-(hydroxyamino)-3-oxopropyl]benzyl}amino)cyclopentanecarboxylate (Example 7)(40 mg) was stirred with lithium hydroxide (40 mg, 15 mmol) in THF (1 mL) and water (1 mL) at 45° C. for 36 hours. The reaction was concentrated under reduced pressure and the resulting residue purified by Gilson preparative HPLC. The purified carboxylic acid derivative was stirred in dichloromethane:TFA (1 mL, 1:1 v/v) for 1 h at room temperature and the reaction concentrated under reduced pressure. The title compound (3 mg) was isolated as a colourless solid.

$^1H$ NMR (300 MHz, MeOD), 7.47 (2H, d J=7.9 Hz), 7.36 (2H, d J=8.1 Hz), 4.18 (2H, s), 3.01-2.95 (2H, t J=7.5 Hz), 2.38 (4H, m), 1.97-1.59 (6H, m)

Example 9

Cyclopentyl N-{4-[3-(hydroxyamino)-3-oxopropyl]benzyl}-2-methyl-D,L-leucinate

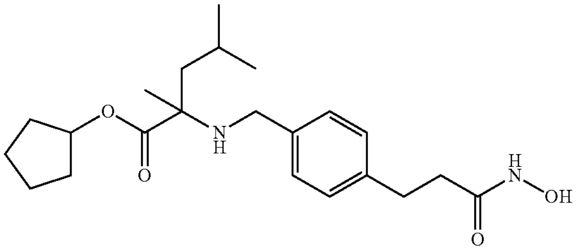 [SMILES: CC(C)CC(C)(NCc1ccc(CCC(=O)NO)cc1)C(=O)OC1CCCC1]

This was made in a similar manner to Example 7 using Intermediate 8 (209 mg, 0.68 mmol) and Intermediate 10 (146 mg, 0.61 mmol) which gave the title compound (200 mg) as a colourless solid. m/z 391.51 $[m+h]^+$.

$^1H$ NMR (300 MHz, MeOD) 7.44 (2H, d J=8.1 Hz), 7.35 (2H, d J=8.1 Hz), 5.38-5.33 (1H, m), 4.21 (1H, d J=12.8 Hz), 4.06 (1H, d, J=12.8 Hz), 2.98 (2H, t J=7.6 Hz), 2.41 (2H, t J=7.6 Hz), 2.04-1.72 (11H, m), 1.68 (3H, s), 0.99 (6H, t J=7.6 Hz).

The following example was made in a similar manner to the title compound of Example 8 using Example 9.

Example 10

N-{4-[3-(Hydroxyamino)-3-oxopropyl]benzyl}-2-methyl-D,L-leucine

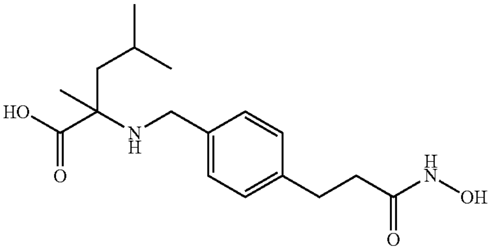 [SMILES: CC(C)CC(C)(NCc1ccc(CCC(=O)NO)cc1)C(=O)O]

m/z 323 $[M+H]^+$. $^1H$ NMR (300 MHz, MeOD), 7.44 (2H, d J=8.1 Hz), 7.35 (2H, d J=8.1 Hz), 4.20 (1H, d J=12.4 Hz), 4.09 (1H, d J=12.6 Hz), 2.97 (2H, t J=7.3 Hz), 2.41 (2H, t J=7.7 Hz), 2.01-1.87 (3H, m), 1.76 (3H, s), 1.01 (6H, t J=6.3 Hz).

Example 11

Cyclopentyl 1-[({6-[(1E)-3-(hydroxyamino)-3-oxoprop-1-en-1-yl]pyridin-3-yl}methyl)amino]cyclohexanecarboxylate

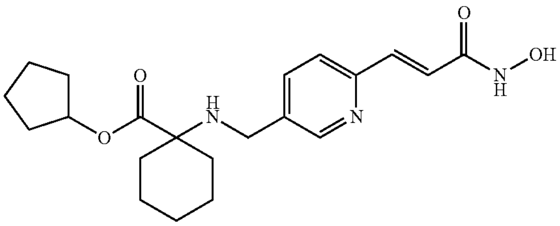 [SMILES: O=C(/C=C/c1ccc(CNC2(C(=O)OC3CCCC3)CCCCC2)cn1)NO]

To a solution of Intermediate 7 (386 mg, 1.83 mmol) and Intermediate 9 (902 mg, 3.02 mmol) in THF (20 mL) was added powdered molecular sieves 4 Å (100 mg) and the resulting mixture was heated at reflux temperature for 12 hours. On cooling to room temperature, sodium borohydride (317 mg, 85 mmol) was added and stirring was continued for 20 minutes. The reaction was quenched with saturated $NH_4Cl$ (50 mL), and then extracted with dichloromethane (3×100 mL). The combined organic layers were dried ($MgSO_4$), concentrated in vacuo and the resulting residue subjected to column chromatography [silica gel, 5% methanol in DCM]. The purified material was dissolved in dichloromethane (20 mL) to which was added 4M HCl in dioxane and the resulting solution was stirred at room temperature for 1 hour. The reaction was quenched with $NaHCO_3$ and extracted with ethyl acetate (2×150 mL). The combined organic layers were dried ($MgSO_4$) and evaporated. The residue was purified by HPLC to give the title compound (80 mg) as a colourless solid, n/z 388.25 $(M+H)^+$. $^1H$ NMR (300 MHz, de-DMSO) 10.95 (1H, br s), 9.43 (1H, br s), 8.65 (1H, d, J=1.7 Hz), 7.92 (1H, dd, J=2.0, 8.0), 7.67 (1H, d, J=8.0 Hz), 7.50 (1H, d, J=15.4 Hz), 6.98 (1H, d, J=15.4 Hz), 5.23 (1H, t, J=5.3 Hz), 4.16 (2H, br s), 2.15-2.30 (2H, m), 1.16-1.96 (16H, m).

Biological Activity

Histone Deacetylase Activity

The ability of compounds to inhibit histone deacetylase activities was measured using the commercially available HDAC fluorescent activity assay from Biomol. In brief, the Fluor de Lys™ substrate, a lysine with an epsilon-amino acetylation, is incubated with the source of histone deacetylase activity (HeLa nuclear extract) in the presence or absence of inhibitor. Deacetylation of the substrate sensitises the substrate to Fluor de Lys™ developer, which generates a fluorophore. Thus, incubation of the substrate with a source of HDAC activity results in an increase in signal that is diminished in the presence of an HDAC inhibitor.

Data are expressed as a percentage of the control, measured in the absence of inhibitor, with background signal being subtracted from all samples, as follows:

$$\%\ \text{activity}=[(S^i-B)/(S^o-B)]\times 100$$

where $S^i$ is the signal in the presence of substrate, enzyme and Inhibitor, $S^o$ is the signal in the presence of substrate, enzyme and the vehicle in which the inhibitor is dissolved, and B is the background signal measured in the absence of enzyme.

$IC_{50}$ values were determined by non-linear regression analysis, after fitting the results of eight data points to the equation for sigmoidal dose response with variable slope (% activity against log concentration of Compound), using Graphpad Prism software.

Histone deacetylase activity from crude nuclear extract derived from HeLa cells was used for screening. The preparation, purchased from 4C (Seneffe, Belgium), was prepared from HeLa cells harvested whilst in exponential growth phase. The nuclear extract was prepared according to the methodology described by J. D. Dignam, *Nucl. Acid. Res.*, 1983, 11, 1475-1489, snap frozen in liquid nitrogen and stored at −80° C. The final buffer composition was 20 mM Hepes, 100 mM KCl, 0.2 mM EDTA, 0.5 mM DTT, 0.2 mM PMSF and 20% (v/v) glycerol.

U937 and HUT Cell Inhibition Assay

Cancer cell lines (U937 and HUT) growing in log phase were harvested and seeded at 1000-2000 cells/well (100 μl final volume) into 96-well tissue culture plates. Following 24 hours of growth cells were treated with compound. Plates were then re-Incubated for a further 72-96 hours before a WST-1 cell viability assay was conducted according to the suppliers (Roche Applied Science) instructions.

Data were expressed as a percentage inhibition of the control, measured in the absence of Inhibitor, as follows:

$$\%\ \text{inhibition}=100-[(S^i/S^o)\times 100]$$

where $S^i$ is the signal in the presence of Inhibitor and $S^o$ s the signal in the presence of DMSO.

Dose response curves were generated from 8 concentrations (top final concentration 10 μM, with 3-fold dilutions), using 6 replicates.

$IC_{50}$ values were determined by non-linear regression analysis, after fitting the results to the equation for sigmoidal dose response with variable slope (% activity against log concentration of compound), using Graphpad Prism software.

p38 MAP Kinase Enzyme Assay

The ability of compounds to inhibit p38 MAPα Kinase activity was measured in an assay performed by Upstate (Dundee UK). In a final reaction volume of 25 μL, p38 MAP Kinase α (5-10 mU) is incubated with 25 mM Tris pH 7.5, 0.02 mM EGTA, 0.33 mg/mL myelin basic protein, 10 mM MgAcetate and [γ-$^{33}$P-ATP](specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

Duplicate data points are generated from a 1/3 log dilution series of a stock solution in DMSO. Nine dilutions steps are made from a top concentration of 101M, and a 'no compound' blank is included. The standard radiometric filter-binding assay is performed at an ATP concentration at, or close to, the Km. Data from scintillation counts are collected and subjected to free-fit analysis by Prism software. From the curve generated, the concentration giving 50% inhibition is determined and reported.

p38 MAP Kinase Cellular Assay: Inhibition of Phosphorylation of MAPKAP2

U937 or HUT78 cells were plated in RPMI 1640, and were incubated at 37° C., 5% $CO_2$ for 18 hours. 10 mM stocks of compounds were diluted media/0.1% DMSO to give a log or semi-log dilution series. The wells for 'no treatment' and 'anisomycin' were treated with 0.1% DMSO only. The cells were incubated at 37° C., 5% $CO_2$ for a further 4 hours. Anisomycin was added to all wells except 'no treatment' at a final concentration of 10 μM. The cells were incubated at 37° C., 5% $CO_2$ for 30 minutes before harvest. Plates were stood on ice whilst harvesting, and all following steps were carried out at 4° C. The cells were pelleted at 1000 rpm for 10 minutes at 4° C., the media aspirated, and the pellet washed with cold PBS. The pellets were lysed in 120 μl of SDS lysis buffer (62.5 mM Tris, pH 6.8, 2% SDS, 10% glycerol, 50 mM DTT, with protease inhibitors and phosphatase inhibitors added according to the manufacturers' recommendations). After 30 minutes on ice, the samples were sonicated for 5 seconds before centrifugation at 13,000 rpm 4° C. for 10 minutes to remove cell debris. 10 μl of the resulting gel samples were loaded per lane on NOVEX 4-12% Bis-Tris MOPS gels. Membranes from western transfer of gels were blotted with anti-phospho MAPKAP2, anti-phospho HSP27 and anti GAPDH according to the manufacturers' Instructions. Signal was visualised using HRP-Hnked anti-rabbit or anti-mouse antibodies, ECL reagent and ECL film. IC50 values for the various compounds were visualised from the resulting photographic images, using both band-shift and signal intensity.

LPS-Stimulation of THP-1 Cells

THP-1 cells were plated in 100 μl at a density of $4\times10^4$ cells/well in V-bottomed 96 well tissue culture treated plates and incubated at 37° C. in 5% $CO_2$ for 16 hours. 2 hours after the addition of the inhibitor in 100 μl of tissue culture media, the cells were stimulated with LPS (*E coli* strain 005:B5, Sigma) at a final concentration of 1 μg/mL and Incubated at 37° C. in 5% $CO_2$ for 6 hours. TNF-α levels were measured from cell-free supernatants by sandwich ELISA (R&D Systems #QTA00B)

HCE-1 Carboxylesterase Assay

Hydrolysis of esters to the corresponding carboxylic acids by hCE-1 can be measured using the following procedure. At zero time, 100 μl of recombinant hCE-1 at a concentration of 6 μg/mL in phosphate assay buffer ($K_2PO_4$ 100 mM, KCl 40 mM, pH 7.4) was added to an equal volume of assay buffer containing 5 μM ester substrate. After thorough mixing, triplicate samples were incubated for 0, 20 or 80 minutes at 37° C. At the appropriate time, hydrolysis was stopped by the addition of 600 μl of acetonitrile. For zero time samples, the acetonitrile was added prior to the enzyme. The samples were analysed for the ester and its corresponding carboxylic acid at room temperature by LCMS (Sciex API 3000, HP1100 binary pump, CTC PAL). Chromatography was based on a MeCN (75×2.1 mm) column and a mobile phase of 5-95% acetonitrile in water/0.1% formic add. Levels of the acid, the hydrolysis product, after 80 minutes are expressed in ng/mL.

Broken Cell Carboxylesterase Assay

Any given compound of the present invention wherein ester conjugate according to the invention may be tested to determine whether it meets the requirement that it be hydrolysed by intracellular esterases, by testing in the following assay.

Preparation of Cell Extract

U937 or HCT 116 tumour cells (~$10^9$) were washed in 4 volumes of Dulbeccos PBS (~1 liter) and pelleted at 525 g for 10 min at 4° C. This was repeated twice and the final cell pellet was re-suspended in 35 mL of cold homogenising buffer (Trizma 10 mM, NaCl 130 mM, $CaCl_2$ 0.5 mM pH 7.0 at 25° C.). Homogenates were prepared by nitrogen cavitation (700 psi for 50 min at 4° C.). The homogenate was kept on ice and supplemented with a cocktail of inhibitors at final concentrations of:

Leupeptin 1 μM
Aprotinin 0.1 μM
E64 8 μM
Pepstatin 1.5 μM
Bestatin 162 μM
Chymostatin 33 μM After clarification of the cell homogenate by centrifugation at 525 g for 10 min, the resulting supernatant was used as a source of esterase activity and was stored at −80° C. until required.

Measurement of Ester Cleavage

Hydrolysis of esters to the corresponding carboxylic acids can be measured using the cell extract, prepared as above. To this effect cell extract (~30 μg/total assay volume of 0.5 mL) was incubated at 37° C. in a Tris-HCl 25 mM, 125 mM NaCl buffer, pH 7.5 at 25° C. At zero time the ester (substrate) was then added at a final concentration of 2.5 μM and the samples were incubated at 37° C. for the appropriate time (usually 0 or 80 minutes). Reactions were stopped by the addition of 3× volumes of acetonitrile. For zero time samples the acetonitrile was added prior to the ester compound. After centrifugation at 12000 g for 5 min, samples were analysed for the ester and its corresponding carboxylic acid at room temperature by LCMS (Sciex API 3000, HP1100 binary pump, CTC PAL). Chromatography was based on a MeCN (75×2.1 mm) column and a mobile phase of 5-95% acetonitrile in water/0.1% formic acid. Rates of hydrolysis are expressed in pg/mL/min.

Cell Accumulation Assay

Cells ($8\times10^4$/mL) were incubated at 37° C. in culture medium containing 6 μM compound in a 5% (v/v) $CO_2$-humidified atmosphere. Incubations were terminated after 6 h by centrifugation of 25 mL aliquots of the cell suspension at 300 g for 5 minutes at 4° C. 0.2 mL samples of the culture media supernatants were added to 4 volumes of acetonitrile (Sigma-Aldrich). After decanting the supernatant, the residual cell pellet ($2\times10^6$ cells) was extracted into 1 mL of acetonitrile. Samples were then analysed for the ester and acid metabolite at room temperature by LC/MS/MS (Sciex API3000). Chromatography was based on a MeCN (75×21 mm) column with a 5-95% (v/v) acetonitrile, 0.1% (v/v) formic acid mobile phase. For the zero time samples, the cell suspension was chilled and centrifuged as soon as the ester had been added and then extracted into acetonitrile as described. Levels in cells are expressed as ng/mL.

TABLE 1

| Compound | Inhibition of P38 (IC50 nM) | Inhibition of phosphorylation of MAPKAP-2 in U937 cells (IC50, nM) | Ratio cell IC50s to enzyme IC50 | Cleavage by HCE-1 | Cleavage by cell lysate from U937 cells pg/mL/min | Cell accumulation in U937 cells at 6 hours (ng/mL) |
|---|---|---|---|---|---|---|
| 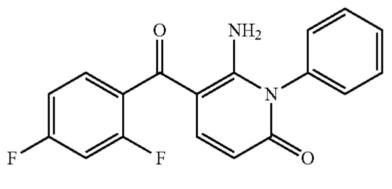 [SMILES: Nc1c(C(=O)c2ccc(F)cc2F)ccc(=O)n1-c1ccccc1] Compound I (parent) | 50 | 300 | 6 | NA | NA | NA |

TABLE 1-continued

| Compound | Inhibition of P38 (IC50 nM) | Inhibition of phospho-rylation of MAPKAP-2 in U937 cells (IC50, nM) | Ratio cell IC50s to enzyme IC50 | Cleav-age by HCE-1 | Cleavage by cell lysate from U937 cells pg/mL/ min | Cell accumu-lation in U937 cells at 6 hours (ng/mL) |
|---|---|---|---|---|---|---|
| 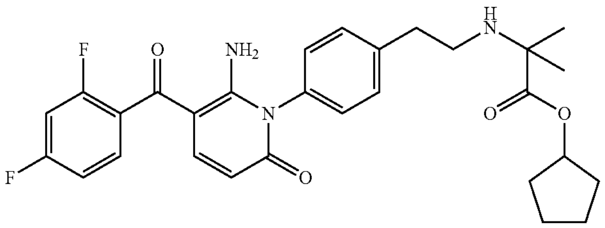 [SMILES: CC(C)(NCCc1ccc(-n2c(N)c(C(=O)c3ccc(F)cc3F)ccc2=O)cc1)C(=O)OC1CCCC1] Example 1 | Ester 50 Acid 50 | 10 | 0.2 | 198 | 165 | 987 |

Table 1 shows that the acid of Example 1 has a similar IC50 in the enzyme assay to the parent compound (Compound I): (WO 03/076405) indicating that binding to the enzyme has not been disrupted by attachment of the esterase motif. Di-substituted compounds, e.g. Example 1, are hydrolysed by hCE-1 and as a consequence the acid accumulates in cells. This accumulation of acid results in Example 1 being significantly more potent than the parent compound in the cellular assay. These data highlight the potency benefit that can be achieved by the attachment of the esterase motif and the resulting cellular accumulation of the corresponding acid.

TABLE 2

| Compound | Inhibition of phospho-rylation of MAPKAP-2 in U937 cells (IC50, nM) (monocyte cell line) | Inhibition of phospho-rylation of MAPKAP-2 in HUT 78 cells (IC50, nM) (non-monocyte cell line) | Ratio IC50s in HUT 78 to U937 cells | Accumu-lation in U937 cells (ng/mL) | Accumu-lation in HUT 78 cells (ng/mL) |
|---|---|---|---|---|---|
| Parent Compound I | 300 | 450 | 1.5 | NA | NA |
| Example 1 | 10 | 1000 | 100 | 987 | 3 |
| 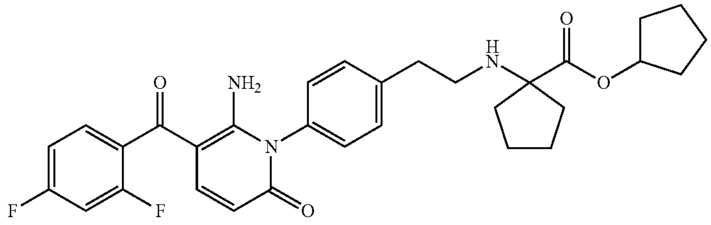 [SMILES: Nc1c(C(=O)c2ccc(F)cc2F)ccc(=O)n1-c1ccc(CCNC2(C(=O)OC3CCCC3)CCCC2)cc1] Example 3 | 100 | 10000 | 100 | ND | ND |

Table 2 shows that the parent compound (Compound I) is equipotent in monocytic and non monocytic cell lines whereas Examples 1 and 3 are 100 times more potent in the monocytic cell line. Example 1 only accumulates in the monocytic cell line showing that cell selectivity is achieved by the attachment of an esterase motif that is only cleaved in the monocytic cell line.

TABLE 3

| Compound | Inhibition of phosphorylation of MAPKAP-2 in U937 cells (IC50, nM) (monocyte cell line) | Inhibition of phosphorylation of MAPKAP-2 in HUT 78 cells (IC50, nM) (non-monocyte cell line) | Ratio IC50s in HUT 78 to U937 cells |
|---|---|---|---|
| 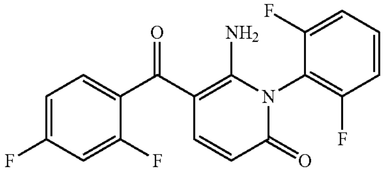 [SMILES: Nc1c(C(=O)c2ccc(F)cc2F)ccc(=O)n1-c1c(F)cccc1F] Parent Compound II | 10 | 10 | 1 |
| 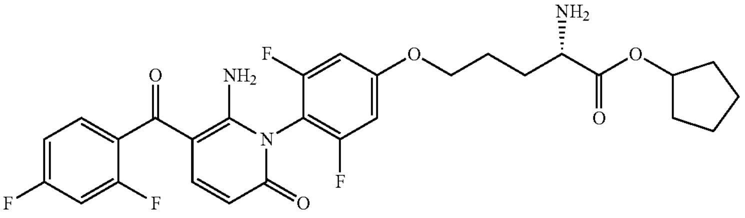 [SMILES: Nc1c(C(=O)c2ccc(F)cc2F)ccc(=O)n1-c1c(F)cc(OCCC[C@H](N)C(=O)OC2CCCC2)cc1F] Compund III | 1 | 1 | 1 |
| 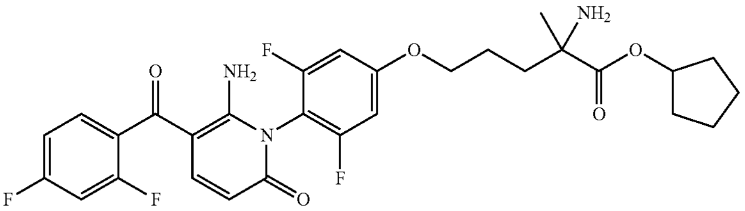 [SMILES: CC(N)(CCCOc1cc(F)c(-n2c(N)c(C(=O)c3ccc(F)cc3F)ccc2=O)c(F)c1)C(=O)OC1CCCC1] Example 5 | 5 | 100 | 20 |

Table 3 indicates that a C-linked dialkyl compound (Example 5) is macrophage selective whereas the parent compound (Compound II; WO 03/076405) and a compound (Compound III; WO 2007/129036) lacking an alkyl group at the alpha carbon of the amino acid derivative are not. This illustrates that macrophage selectivity can be achieved by the Introduction of a second substituent at the alpha carbon of the amino acid ester motif.

TABLE 4

| Compound | Inhibition of HDAC (IC50 nM) | Inhibition of proliferation in U937 cells | Ratio cell IC50s to enzyme IC50 | Cleavage by HCE-1 |
|---|---|---|---|---|
| 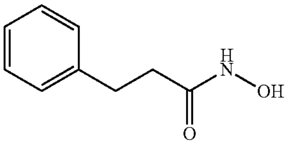 [SMILES: O=C(CCc1ccccc1)NO] Parent Compound IV | 2600 | 13% @ 10 μM | >3.85 | NA |

TABLE 4-continued

| Compound | Inhibition of HDAC (IC50 nM) | Inhibition of proliferation in U937 cells | Ratio cell IC50s to enzyme IC50 | Cleavage by HCE-1 |
|---|---|---|---|---|
| 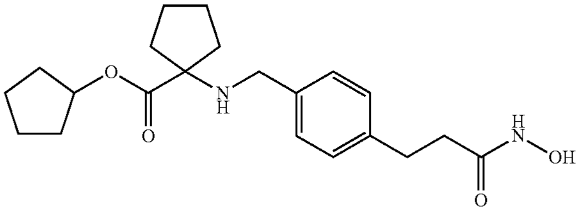 [SMILES: O=C(CCc1ccc(CNC2(C(=O)OC3CCCC3)CCCC2)cc1)NO] Example 7 | Ester 4200 Acid 6120 | 180 | 0.043 | >12600 pg/mL/min |
| 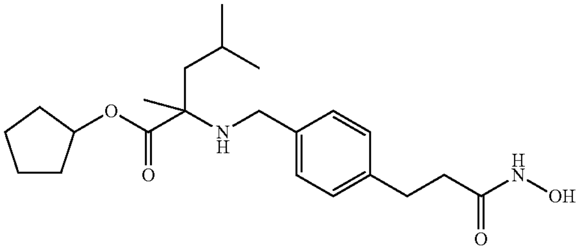 [SMILES: CC(C)CC(C)(NCc1ccc(CCC(=O)NO)cc1)C(=O)OC1CCCC1] Example 9 | 4900 6242 | 190 | 0.04 | ND |

Table 4 shows that the acid of Examples 7 and 9 have similar IC50s in the enzyme assay to the parent compound (Compound IV): indicating that binding to the enzyme has not been disrupted by attachment of the esterase motif. DI-substituted compounds, e.g. Example 7, are hydrolysed by hCE-1 and as a consequence the acid accumulates in monocytic cells. This accumulation of acid results in Examples 7 and 9 being significantly more potent than the parent compound in the cellular assay. These data highlight the potency benefit that can be achieved by the attachment of the esterase motif.

TABLE 5

| Compound | Inhibition of HDAC (IC50 nM) | Inhibition of proliferation in U937 cells (IC50 nM) | Inhibition of proliferation in HUT 78 cells (IC50 nM) | Ratio IC50s in HUT 78 to U937 cells |
|---|---|---|---|---|
| 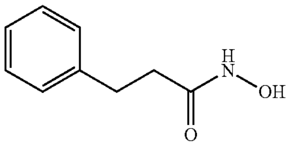 [SMILES: O=C(CCc1ccccc1)NO] Parent Compound IV | 2600 | 13% @ 10 μM | 10% @ 10 μM | ~1 |
| 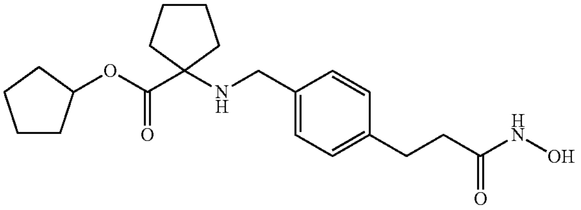 [SMILES: O=C(CCc1ccc(CNC2(C(=O)OC3CCCC3)CCCC2)cc1)NO] Example 7 | Ester 4200 Acid 6120 | 180 | 6200 | 34 |

TABLE 5-continued

| Compound | Inhibition of HDAC (IC50 nM) | Inhibition of proliferation in U937 cells (IC50 nM) | Inhibition of proliferation in HUT 78 cells (IC50 nM) | Ratio IC50s in HUT 78 to U937 cells |
|---|---|---|---|---|
| 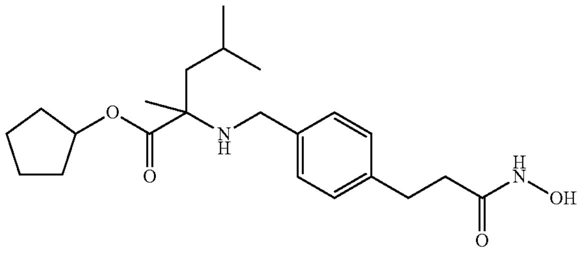 [SMILES: CC(C)CC(C)(NCc1ccc(CCC(=O)NO)cc1)C(=O)OC1CCCC1] Example 9 | 4900 6242 | 190 | 5500 | 30 |

Table 5 shows that the parent compound (Compound IV) has similar potencies in monocytic (U937) and non monocytic (Hut78) cell lines whereas Examples 7 and 9 are 30 times more potent in the monocytic cell line than the non-monocytic cell line. This illustrates that a second substituent at the alpha position of the amino acid motif confers macrophage selectivity on the compounds.

The invention claimed is:

1. A compound which is:

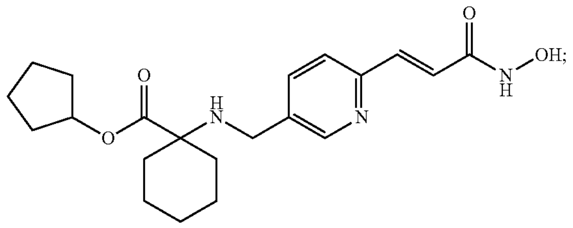 [SMILES: O=C(/C=C/c1ccc(CNC2(C(=O)OC3CCCC3)CCCCC2)cn1)NO]

or a pharmaceutically acceptable salt thereof.

2. A compound which is:

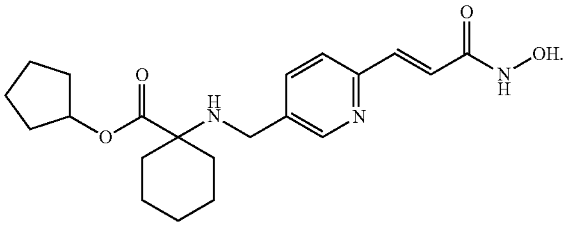 [SMILES: O=C(/C=C/c1ccc(CNC2(C(=O)OC3CCCC3)CCCCC2)cn1)NO]

3. A pharmaceutical composition comprising the compound or pharmaceutically acceptable salt according to claim 1 and a pharmaceutically acceptable carrier or excipient.

4. A pharmaceutical composition comprising the compound according to claim 2 and a pharmaceutically acceptable carrier or excipient.

* * * * *